United States Patent [19]

Bartolini et al.

[11] Patent Number: 5,583,142

[45] Date of Patent: Dec. 10, 1996

[54] ANALGESIC AND NOOTROPIC DRUGS

[75] Inventors: Alessandro Bartolini, Montevarchi; Carla Ghelardini, Pistoia; Alberto Giotti, Fucecchio; Fulvio Gualtieri, Scandicci; Serena Scapecchi, Sesto Fiorentino; Gino Toffano, Montegrotto Terme, all of Italy

[73] Assignee: Fidia S.p.A., Abano Terme, Italy

[21] Appl. No.: 369,761

[22] Filed: Jan. 6, 1995

Related U.S. Application Data

[63] Continuation-in-part of PCT/EP93/01743 Jul. 6, 1993.

[30]  Foreign Application Priority Data

Jul. 8, 1992 [IT] Italy .................................. MI92A1659

[51] Int. Cl.$^6$ ......................... A61K 31/44; C07D 451/02
[52] U.S. Cl. .......................... 514/304; 546/124; 546/127; 546/128; 546/129; 546/130
[58] Field of Search ..................... 546/124, 127, 546/128, 129, 130; 514/304

[56] References Cited

FOREIGN PATENT DOCUMENTS

| | | |
|---|---|---|
| 1289429 | 2/1962 | France . |
| 1179900 | 2/1970 | United Kingdom . |
| 9216528 | 10/1992 | WIPO . |

OTHER PUBLICATIONS

W. Schultz et al. Eine Neue Methode Zur Technischen Darstellung von Tertiaren etc., Arzneimittel Forschung. Drug Research vol. 26, No. 5A, 1976 Aulendorf De pp. 960–974.

Louis S. Harris et al., Narcotic–Antagonist Analgesics: Interactions With Cholinergic Systems, May 9, 1969, The Journal of Pharmacology and Experimental Therapeutics, vol. 1969, No. 1, pp. 17–22.

A. Bartolini, et al., Antinociception Induced By Systemic Administration of Local Anaesthetics Depends On a Central Cholinergic Mechanism., Br. J. Pharmac (1987), 92, 711–721.

A. Bartolini, et al., Role of Muscarinic Receptor Subtypes in Central Antinociception, Br. J. Pharmacol. (1992) 105, 77–82.

Von W. Schulz, et al., Eine Neue Methode zur technischen Darstellung von tertiaren and quartaren d,1–Tropasaureenstern einiger N–substituieter Northropan–bzw Granatan 3–ole, Arzeneim–Forsch (Drug. Res.) 26, Nr. 5a (1976), 960–974.

J. C. Szerb et al., Release of [$^3$H] Acetylcholine From Rat Hippocampal Slices: Effect of Septal Lesion and of Graded Concentrations of Muscarinic Agonists and Antagonists, Brain Resarch, 128 (1977) 285–291.

Roman Pohorecki et al., Effects of Selected Muscarinic Cholinergic Antagonists on [$^3$H] Acetylcholine Release From Rat Hippocampal Slices, 1987, The Journal of Pharmacoclogy and Experimental Therapeutics, 1987, vol. 244, No. 1, 213–217.

Paul A. Lapchak, et al., Binding sites for [$^3$H] 116 and effect of AF–DX 116 on endogenous acetylcholine release from rat brain slices, Brain Research, 496 (1989) 285–294).

Torocsik et al., Presynaptic Effects Of Methoctramine On Release Of Acetylcholine, 1991, Neuropharmacology, vol. 30, No. 3 pp. 293–298.

J. de Belleroche et al., Dopamine Inhibition of the Release of Endogenous Acetylcholine from Corpus Striatumane Cerebral Cortex In Tissue Sliceds and Synaptosomes: A Presynaptic Response?, 1982, J. Neurochem., vol. 39, No. 1, pp. 217–222.

D. Fage et al., Opposing effects of D–1 and D–2 receptor antagonists on acetylcholine levels in the rat striatum, 1986, European Journal of Pharmacology, 129, pp. 359–362.

D. H. Thor, et al., Social Memory of the Male Laboratory Rat, Journal of Comparative and Physiological Psychology, vol. 96, No. 6, 1000–1006, 1982.

O. Vainio et al., Sedative and analgesic effects of medetomidine in dogs, 1989, J. Vet. Pharmacol Ther. 12, 225–231 (1989).

(List continued on next page.)

*Primary Examiner*—Sharon Gibson
*Assistant Examiner*—Catherine Kilby Scalzo
*Attorney, Agent, or Firm*—Kenyon & Kenyon

[57] ABSTRACT

Compounds of general formula:

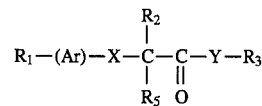

where:

Ar=phenyl or beta-naphtyl, or aromatic heterocyclic 6-membered ring containing one or two nitrogen atoms;

$R_1$=one or more substituents of the Ar nucleus, preferably in para position, and selected out of the group consisting of H, $CH_3$, $CH_2$—CH—$(CH_3)_2$, O—$CH_3$, Cl, F, Br, $CF_3$, $NH_2$, S—$CH_3$, CN, $NO_2$ $R_2$=H, $CH_3$, $C_2H_5$, $CH(CH_3)_2$;

$R_3$=

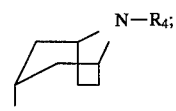

Where $R_4$=H, $CH_3$, $C_2H_5$ $R_5$=H, $CH_3$

X=none O, S, NH, $NCH_3$, —CH=CH—, —C≡C—

Y=O, NH, both in the racemic Form and in the isomeric enantiomeric forms, which produce a nootropic effect, i.e. memory enhancement and learning facilitation, as well as an analgesic effect.

8 Claims, 8 Drawing Sheets

OTHER PUBLICATIONS

J. L. Vaught, et al., A Comparison of the Antinociceptive Responses to the Gaba–Receptor Agonists Thip and Baclofen, Neuropharmacology, vol. 24, No. 3, pp. 211–216, 1985.

Daniela Parolaro, et al., Effect of Intracerebroventricular Administration of Morphine Upon Intestinal Motility in Rat and its Antagonism with Naloxone, European Journal of Pharmacology, 46, 1977, 329–338.

L. F. Berhenke, et al., Some Aryloxyaliphatic Acids, 1952, Journal Am. Chem. Soc., 73, 4458.

C. H. Fawcett, et al., Ann Appl. Biol. 43, 342–354 (1955).

D. C. Abbott, et al., Addition and Substitution with the Bromine Cation in Aqueous Solution, J. Chem. Soc. 2934, 1952.

C. A. Bischoff, et al., Berichte, 1900, 33, 1386.

Berndt Sjoberg, Arkiv Kemi 15, 397–401 (1960).

Giancarlo Bettoni, et al., Stereospecificity of the Chloride Ion Channel: The Action of Chiral Clofibric Acid Analogues, J. Med. Chem., 1987, 30, 1267–1270.

A. Berthold, et al., Arnzneim Forsch., 17, 719 (1967).

Friedrich Nerdel, et al., Chem. Ber., 87, 217, 1954.

Bartolini, et al., i.c.v. AFDX–116 induces analgesia only when administered at very low doses, TIPPS Suppl. IV 99 (1989).

Gualtieri, et al., Muscarinic $M_1$ contrary to $M_2$ antagonists do not induce analgesia, TIPPS Supp. IV 99 (1989).

C. Ghelardini, et al., Investigation into atropine–induced antinociception, Br. J. Pharmacol. (1990), 101, 49–54.

*P<0.05 IN COMPARISON WITH (−)-SCOPOLAMINE TREATED MICE

* P<0.01 IN COMPARISON WITH SALINE TREATED RATS

FIG. 7Bis

AMPHET. = AMPHETAMINE
MORPH. = MORPHINE

\* $P<0.05$ IN COMPARISON WITH CONTROLS

ANALGESIC AND NOOTROPIC DRUGS

This application is a continuation-in-part of International Application PCT/EP93/01743 having an international filing date of Jul. 6, 1993.

FIELD OF THE INVENTION

The present invention refers to a new class of compounds including derivatives of α-aryl substituted alkanoic acids, characterized by the presence of a tropanyl group bound to the carboxyl through an ester or amidic linkage.

The claimed compounds produce a nootropic effect (i.e. learning facilitation and memory enhancement) as well as an analgesic effect. Therefore, they are suitable for treating cognitive deficits and various types of pain in humans.

PRIOR ART

Cholinergic-mediated central neurotransmission has a number of important functions; in particular, it plays a major role in cognitive processes (learning and memory) and pain central perception. The role of the cholinergic system in cognitive processes is amply documented by scientific literature: it is enough to quote the paper by Bartus et al. in Science 217, 408–417 (1982).

The role of the cholinergic system in antinociception is less documented [Harris et al., J. Pharmac. Exp. Ther., 169, 17–22 (1969); Bartolini et al., Br. J. Pharmacol., 92, 711–721 (1987); Bartolini et al., Br. J. Pharmacol., 105, 77–82 (1992)]. However, this does not mean that the experimental results supporting it are less reliable.

It would, therefore, be extremely useful to use cholinomimetic drugs capable of crossing the blood-brain barrier both to enhance cognitive processes and to reduce pain. However, the said drugs, though efficacious, have never been used due to their unbearable side effects both of central (tremors, etc.) and peripheral origin (bradycardia, sialorrhoea, diarrhoea, eyesight disorders, etc.).

Recent results [Bartolini et al., Br. J. Pharmac., 92, 711–721 (1987); Bartolini et al., TIPS Suppl. IV 99 (1989); Gualtieri et al., TIPS Suppl. IV, 99 (1989); Ghelardini et al., Br. J. Pharmacol., 101, 49–54 (1990)], provided evidence that the functioning of the central cholinergic system can be improved in laboratory animals without inducing physiologically non-programmed activations of said system. Pain threshold was increased and cognitive processes were improved without untoward side effects.

This results was obtained by drugs suppressing the physiological counterreaction mechanism of the cholinergic synaptic autoreceptor and blocking other inhibitory presynaptic heteroreceptors located on the cholinergic synapse itself. Unfortunately, the selective antagonists of presynaptic muscarinic autoreceptors already known, which were utilized by us to obtain several of the aforesaid results, are incapable of crossing the blood-brain barrier and, therefore, must be administered by intracerebroventricular route (ADFX-116, Metoctramine. AQRA-741. UK3138). Conversely, other molecules capable of crossing the blood-brain barrier (such as, for example, some local anaesthetics: procaine, lidocaine, bupivacaine, some antiarrhythmic agents: mexyletine, tocainide, procainamide, and attopine administered at a very low dose), which, too, antagonize the presynaptic muscarinic autoreceptor, proved to be little selective as well as little efficacious.

Collectively, the aforesaid studies provided the basis for the discovery of a mechanism allowing an increase in cholinergic system functioning by pharmacological means, without untoward side effects.

SUMMARY OF THE INVENTION

Object of the present invention, is the synthesis of new chemical structures capable of easily crossing the blood-brain barrier and selectively inhibiting the presynaptic autoreceptors.

The compounds under the present invention may be represented as per the following general formula:

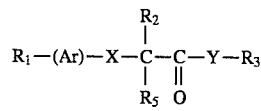

where:
Ar=phenyl or beta-naphtyl, or aromatic heterocyclic 6-membered ring containing one of two nitrogen atoms;
$R_1$=one or more substituents of the Ar nucleus;
preferably in papa position, and selected out of the group consisting of H, $CH_3$, $CH_2$—$CH(CH_3)_2$, O—$CH_3$, Cl, F, Br, $CF_3$, $NH_2$, S—$CH_3$, CN, $NO_2$;
$R_2$=H, $CH_3$, $C_2H_5$, $CH(CH_3)_2$;
$R_3$=

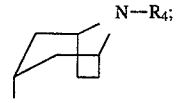

where $R_4$=H, $CH_3$, $C_2H_5$;
$R_5$=H, $CH_3$;
X=none, O, S, NH, $NCH_3$, —CH=CH—, —C≡C—;
Y=O, NH.

The compounds of the invention, characterized by the presence of a tropanyl (or tropanyl like) group, have nootropic effect as well an analgesic effect.

These compounds differentiate from the tropanyl containing compounds disclosed by British Patent 1.179.900, French Patent 1.289.429 and by W. Schulz et al. in Arzneim-Forsch 26 n. 5, pages 960–74 (1976) which are characterized by being tropic acid esters.

DESCRIPTION OF THE INVENTION

The claimed invention contemplates the discovery of new chemical structures capable of increasing the central and peripheral cholinergic system physiological functioning and, therefore, through said selective mechanism of action, capable of facilitating learning, enhancing memory and raising the threshold of pain. The following list reports some of the most significant papers supporting the role of the autoreceptor [Szerb et al., Brain Res., 128, 285 (1977); Pohorecki et al., J. Pharmacol. Exp. Ther., 244, 213 (1987); Lapchak et al., Brain Res. 496, 285 (1989); Törocsik and Vizi, Neuropharmacol., 30 (3) 293 (1991)] and of presynaptic heteroreceptors [Debelloroche et al., J. Neurochem., 39, 217 (1982); Fage and Scotton, Eur. J. Pharmacol., 129, 359 (1986)] in the modulation of endogenous acetylcholine liberation.

BRIEF DESCRIPTION OF THE DRAWINGS

The tested products referred in the figures are identified by monograms which are reported in table 9.

THERAPEUTIC ACTION

The claimed compounds exert both a nootropic and an analgesic action.

The nootropic action (learning facilitation, memory enhancement, intelligence booster, cognition activation) was assessed both in mouse and in rat by the two following methods: the mouse was tested by the passive avoidance method, using the so-called light-dark box. A painful stimulus, i.e. an electrically-evoked shock through the animal paws, and an unpleasant but not painful stimulus (mice fall into a water-ice mixture ensuing a sudden dark box floor opening) were used. A non-painful stimulus was required because the data referred to learning had not to be untruthfully negative due to the analgesic action of the claimed molecules. The painful stimulus (electric shock), like the unpleasant but not painful one, was effective at the interval of doses at which the claimed molecules were clearly nootropic but not yet analgesic. Independently of the type of stimulus used, the procedure consists of two experimental phases denominated, respectively, Training and Retention, the latter being carried out 24 hrs after the former. The first phase is meant to measure the time taken by mice to pass from the light box to the dark one where they like to go but where punishment is inflicted, i.e. fall into iced water or electric shock. The second phase serves the purpose of evaluating the animals capability to remember an unpleasant event occurred 24 hrs before. To this purpose the time taken by mice to enter the dark box is measured again: the longer the time recorded in the second day when compared with the first (Retention minus Training), the higher the mice learning and memorizing capabilities.

All claimed molecules were thus found significantly to improve the cognitive processes, i.e. learning and memory, of animals whose amnesia had been induced by drugs (scopolamine, dicyclomine ) and by hypoxic treatment (8-min exposure to an atmosphere of 95% nitrogen and 5% oxygen).

Furthermore they proved to be as active as and even more efficacious than the nootropic drugs taken as reference, such as piracetam and physostigmine.

Figure 1:
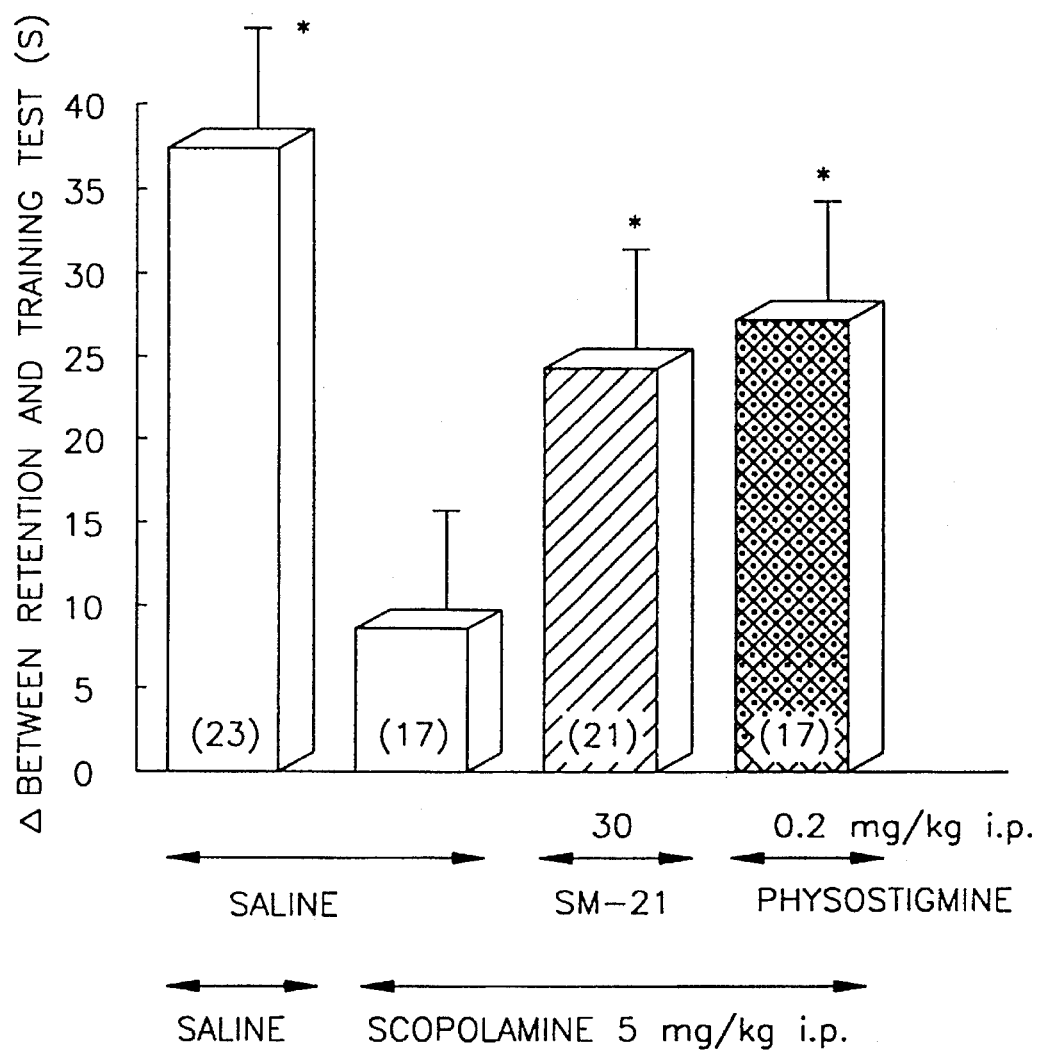
FIG. 1 shows the effect of SM-21 on amnesia induced by scopolamine in mouse passive avoidance test: comparison with physostigmine.
Figure 2:
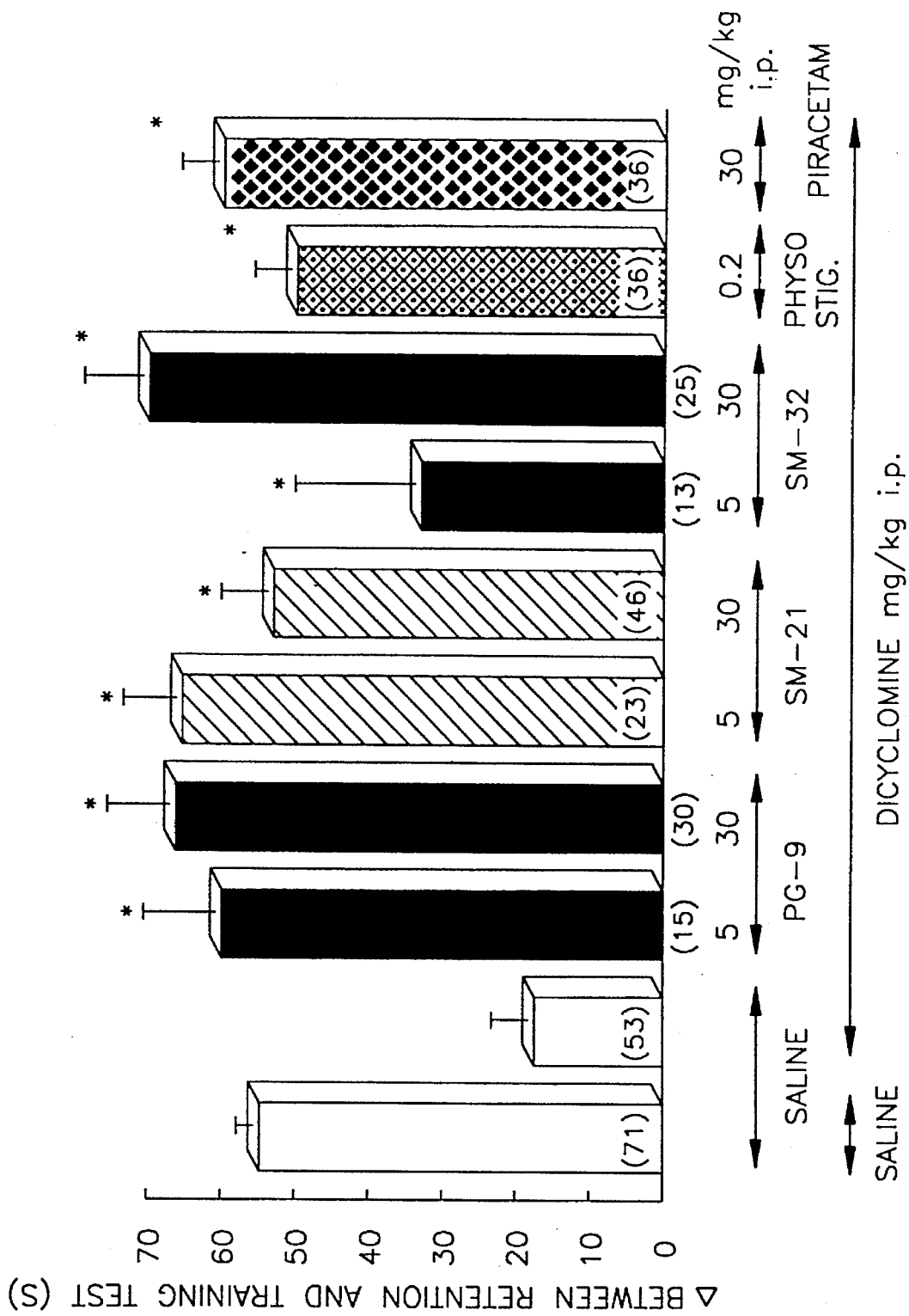
FIG. 2 shows the effect of PG-9, SM-21 and SM-32 on amnesia induced by the muscarinic M1 antagonist dicyclomine in mouse passive-avoidance test: comparison with piracetam and physostigmine.
Figure 3:
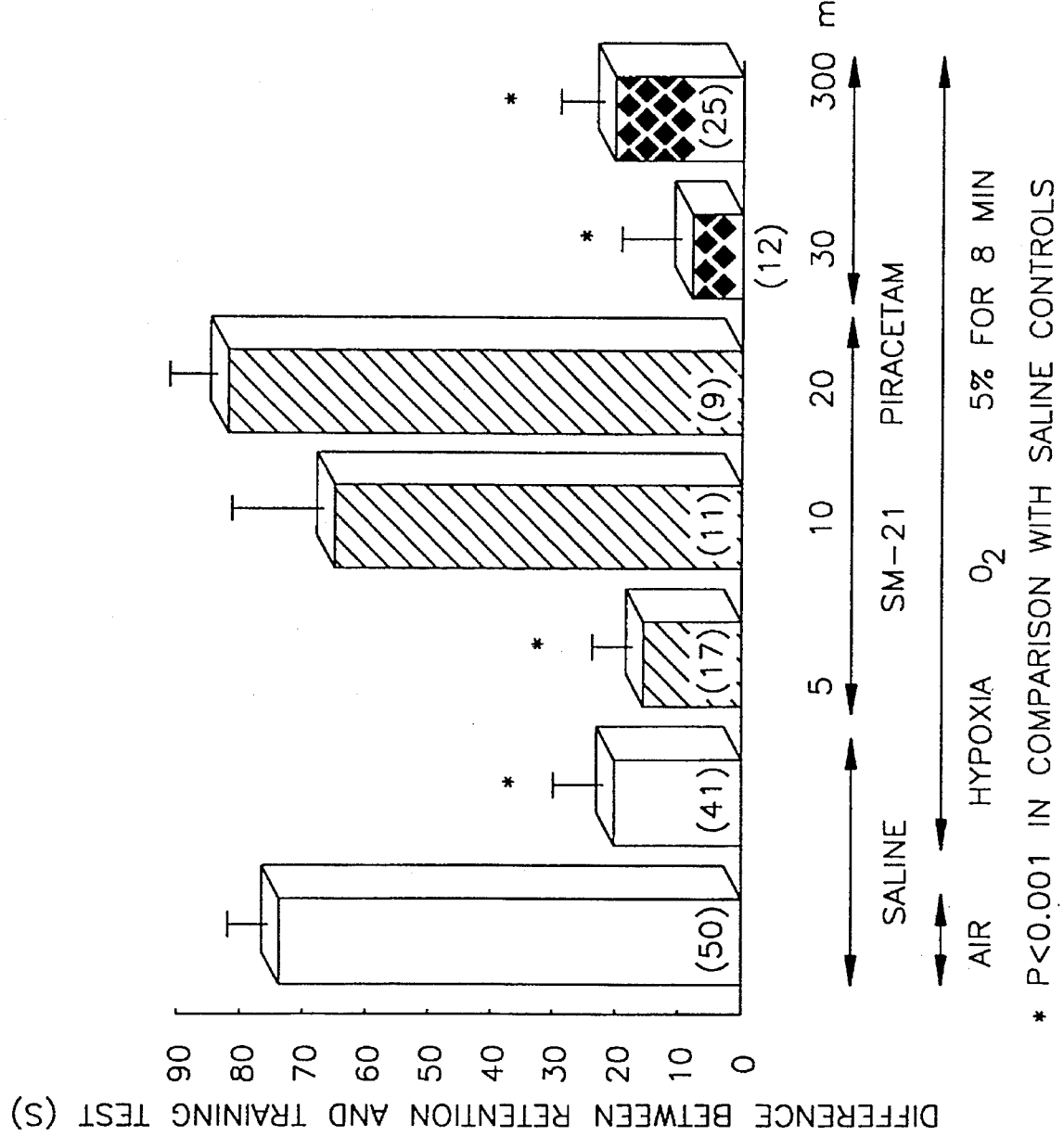
FIG. 3 shows the effect of SM-21 on amnesia induced by hypoxia in mouse passive avoidance test: comparison with piracetam.

FIGS. 1, 2, and 3 show the effect of some of the claimed compounds in comparison with physostigmine and Piracetam.

FIG. 1 shows the antagonism of scopolamine-induced amnesia by SM-21 (product of the invention, see table 9) and physostigmine. The test was runned as follows:

(−)-scopolamine HBr was administered 20 min before training test. SM-21 maleate and physostigmine sulphate were administered immediately after training test.

Punishment shock: COLD WATER BATH

Retention test was performed 24 h after training test. Vertical lines give s.e. mean. In parentheses the number of mice.

Analogously, FIG. 2 shows the antagonism of dicyclomine-induced amnesia by SM-21, PG-9, SM-32, physostigmine, and Piracetam.

The test was runned as follows:

PG-9 maleate, SM-21 maleate, SM-32 oxalate and physostigmine sulphate (physostig.) were administered 20 min. before training. Piracetam was administered 30 min before training. Dicyclomine was injected immediately after training test.

Punishment shock: COLD WATER BATH

Retention test was performed 24 h after training test. Vertical lines give s.e. mean. In parentheses the number of mice.

FIG. 3 shows the effect of SM-21 administered at various doses (5, 10, and 20 mk/kg i.p.) on the amnesia induced by hypoxia. The test was runned as follows:

SM-21 maleate and piracetam were administered 20 min and 30 min before hypoxia respectively. Mice were substituted to hypoxia immediately before training session.

Punishment shock: 0.15 mA, 1 s.

Retention test was performed 24 h after training test. Vertical lines give s.e. mean. In parentheses the number of mice.

In this case, Piracetam (30 to 300 mg/kg i.p. ), unlike SM-21, is inactive. In fact, Piracetam can antagonize the amnesia induced by hypoxia only if the degree of hypoxia and, consequently, of the resulting amnesia, is considerably lower than envisaged in the experimental protocol.

The nootropic effect in rat was evaluated by the social learning method described by Thor and Holloway (J. Comp. Physiol. Psychol., 96, 1000–1006, 1982). According to this method, a young rat (4 weeks old) was taken to the cage of an adult rat (3 months old) for 5 min. The time spent by the adult rat to explore the young rat was measured within the said 5-min period. After 24 hrs, the adult rat had, for the second time, the same experience: the same young rat was taken again to the adult rat's cage. The difference in social learning times between the first and the second exposures is directly proportional to the degree of memorization. In fact, the shorter the time of social learning in the second exposure, the better the recollection of the first event. Obviously, nootropic drugs increase the difference in social learning times between the two phases.

Figure 4:
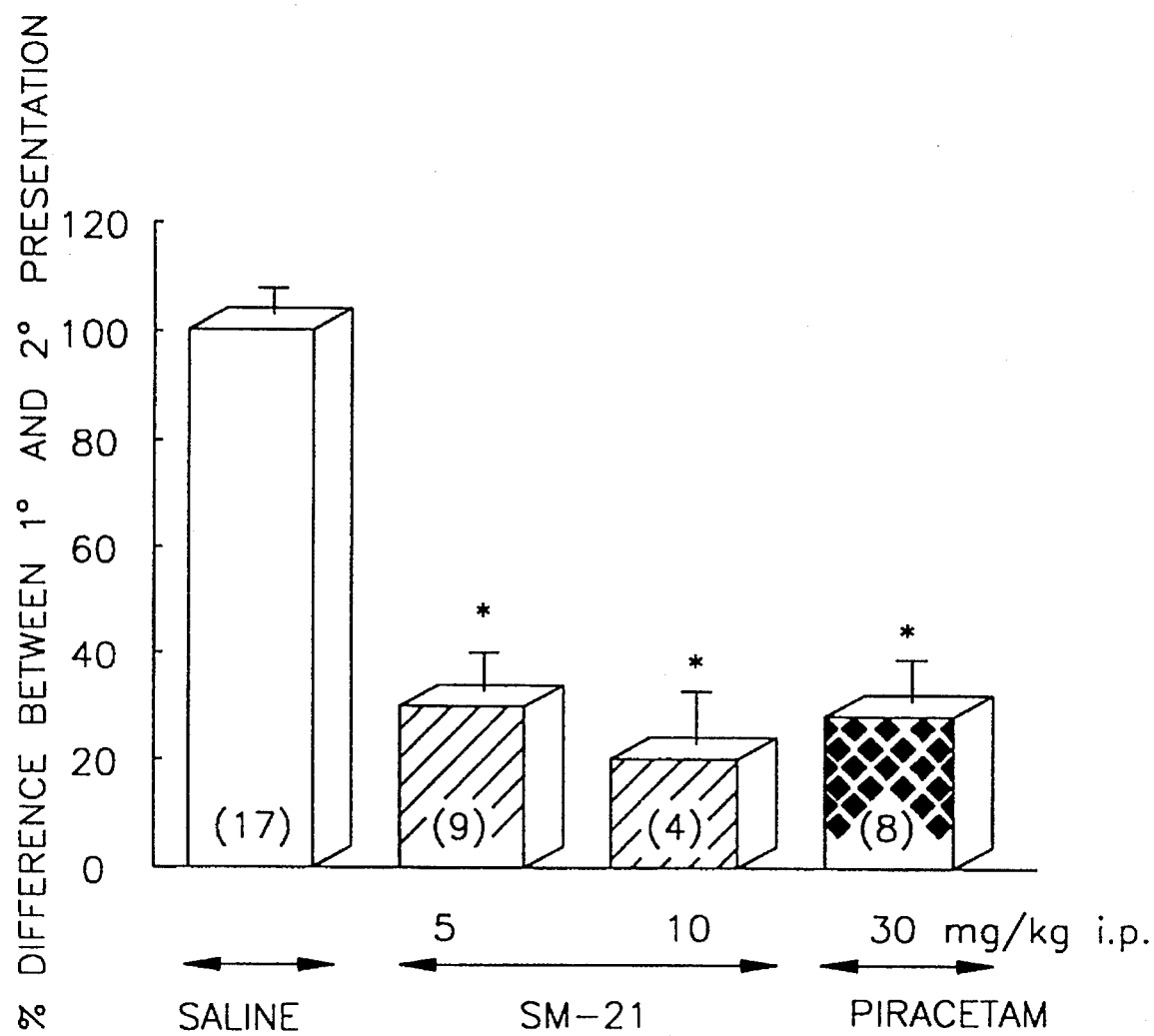
FIG. 4 shows the effect of SM-21 on social-learning test in rats: comparison with piracetam.

FIG. 4 shows the effect of two doses of SM-21 (5 and 10 mg/kg i.p. ) and of Piracetam (30 mg/kg i.p. ) in social learning test.

The test was runned as follows:

SM-21 and Piracetam were administered respectively 20 and 30 min before training test. In parentheses the number of rats. Retention test was performed 24 h after training test.

Vertical lines give s.e. mean.

The nootropic action of the two substances is clearly evidenced by the drastic fall in the times taken during the second exposure.

The analgesic action was detected in mouse, rat, guinea pig and dog. The mouse was subjected to hot plate and writhing tests; the rat to tail-flick and paw-pressure tests; the guinea pig to paw-pressure test only; the dog to the test described by Vainio et al. [J. Vet. Pharmacol. Ther., 12, 225–231 (1989)] using an electric stimulation. Consequently, the claimed compounds were tested with pain being induced by stimuli of different nature: thermal (hot plate and tail flick), chemical (writhing by acetic acid), mechanical (paw pressure) and electrical (cutaneous stimulation).

All products tested to detect their antinociceptive activity had been previously tested by the rota-rod test to determine their maximum utilizable dose in analgesic tests. In fact, by this test it is possible to determine the highest dose of drug not impairing the normal performance of animals in a test that simultaneously evaluates motor coordination, equilibrium, resistance to fatigue, and muscle strength. This test is meant to evaluate the capability of mice to stay balanced on a rotating rod [cf. Vaught et al., Neuropharmacology, 24 (3) 211– 216 (1985)].

Table 1 reports the data referred to four reference analgesic compounds and to three compounds under the present invention. The analgesic compounds taken as reference were morphine, diphenhydramine (DFD), clomipramine hydrochloride (Clom.HCl), and ketorolac (Ketor. Tr.), being the most potent analgesics used in clinical practice and belonging to four different classes acting through different mechanisms, i.e. they are active on the opioid, histamine, serotonine, and prostaglandins system, respectively.

The data shown in the Table allowed the determination (last column to the right) of the max. injectable dose of each product—in comparison with physiological saline—not altering the mice performance in the rota-rod test. The calculated doses were those used in the two analgesic tests on mice.

Therefore, the analgesic action of the claimed products can be easily compared with that of the reference drugs, since each product—independently of its mechanism of action—was tested at the max. dose not altering the mice performance in the rota-rod test.

Figure 5:
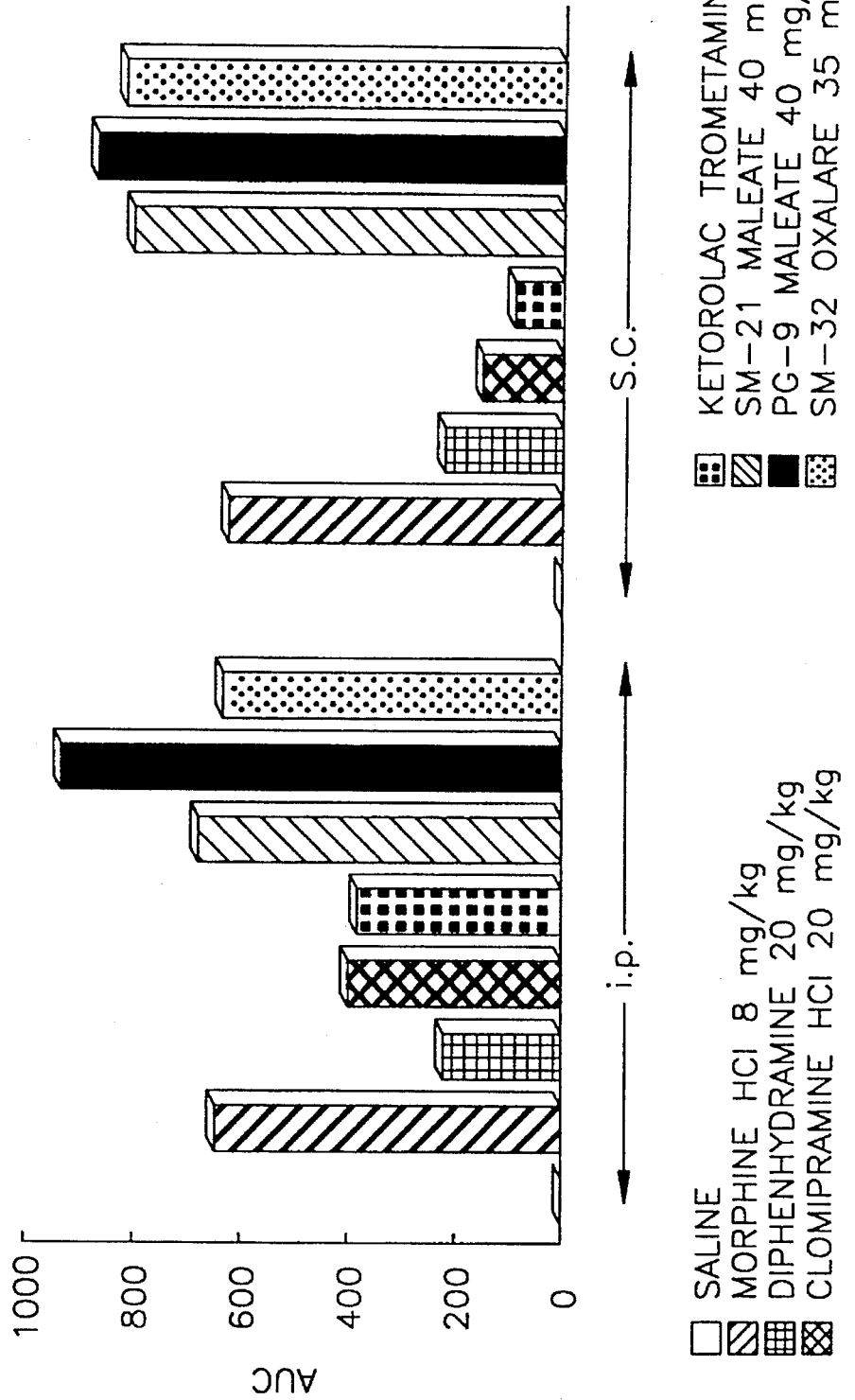
FIG. 5 shows the analgesic effect of SM-21, PG-9 and SM-32 in comparison with four reference analgesic drugs in mouse hot-plate test (52.5° C.)

As shown in Table 2, the claimed products exert their maximum analgesic action tested on the hot plate, 15 min. after administration against the 30 min. taken by morphine. All claimed compounds are efficacious irrespective of their administration route, unlike Ketorolac which is inactive when the administration is s.c. FIG. 5 shows the areas under curve (AUC) where AUC=Area Under Curve (from the administration of the drugs up to 45 min) concerning the analgesic effect measured by the hot-plate test. As may be seen, SM-21 and PG-9 are always more active than all reference analgesics including morphine. SM-32 is more active than the reference compounds when the administration is s.c. and only slightly less active than morphine when the administration is i.p.

A comparison between the main pharmacological characteristics of SM-21, PG-9, SM-32 and of the reference compounds is shown in Table 3. The data reported in the two first columns show that the analgesic efficacy—expressed as maximum analgesic effect and area under curve (analgesia intensity+duration)—of morphine is lower than that of SM-21, PG-9, and SM-32, and much higher than that of the reference products, i.e. diphenhydramine. chlomipramine hydrochloride, and ketorolac). The table also gives the corresponding $ED_{50}$ values. Morphine proves to be the most potent molecule: in fact, the dose (in μmoles/kg) of morphine required to obtain a degree of analgesia equivalent to that of the claimed compounds is three times lower.

Dipehnhydramine and clomipramine hydrochloride show $ED_{50}$ values equivalent to those of the claimed compounds, but a much lower degree of analgesia.

As proved by the $LD_{50}$ values of the last column of Table 3, morphine has the highest therapeutic index.

The claimed molecules, chosen as examples, were also assayed in mice by the writhing test (Table 4). The test is meant to evaluate the products capability to prevent mice writhes ensuing abdominal pains caused by i.p. injection of a 0.6% aqueous solution of acetic acid.

It is to be noted that, in the writhing test, pain is mainly of the inflammatory type (peritonitis from acetic acid) and, consequently, anti-inflammatory analgesics are particularly efficacious. Therefore, no wonder that writhes inhibition by ketorolac is higher than by morphine. As shown in Table 4, PG-9 and SM-32, though less efficacious than ketorolac, are more efficacious than morphine. Conversely, SM-21 is slightly inferior to morphine. In this test too, diphenhydramine and clomipramine hydrochloride are far less efficacious.

As already mentioned, the claimed products were assayed also in rat by the paw-pressure and tail-flick tests.

Both tests were carried out with the max. doses not impairing the rats normal behaviour. In fact, no difference in behaviour appeared on observation, to the extent that researchers, who were unaware of the treatment received by the animals, were unable to distinguish among the various groups. The painful stimulus utilized in the paw-pressure test involved the animal consciousness to a much greater extent than the stimulus used in the tail-flick test, in fact, the type and anatomic localization of the latter mainly involved a spinal response.

Tables 5 and 6 show that, in both tests, morphine is the most active compound, whereas diphenhydramine and PG-9 are inactive. Clomipramine hydrochloride and ketorolac are inactive in tail-flick test and active in the paw pressure one. In the paw-pressure test, SM-21, SM-32, clomipramine hydrochloride and ketorolac produce an almost equivalent analgesia. SM-21 and SM32 are the only molecules that, beside morphine, proved to be active in the tail-flick test.

The above results suggest that morphine, SM-21, and SM-32 are active both on the CNS and the spinal system, and that clomipramine hydrochloride and ketorolac do not act on the latter system.

Both tests on rats were carried out with the max. doses not altering the behaviour of the treated animals.

As shown in Table 7, PG-9 proved to be active in mouse, inactive in rat, and active in guinea pig.

Figure 6:
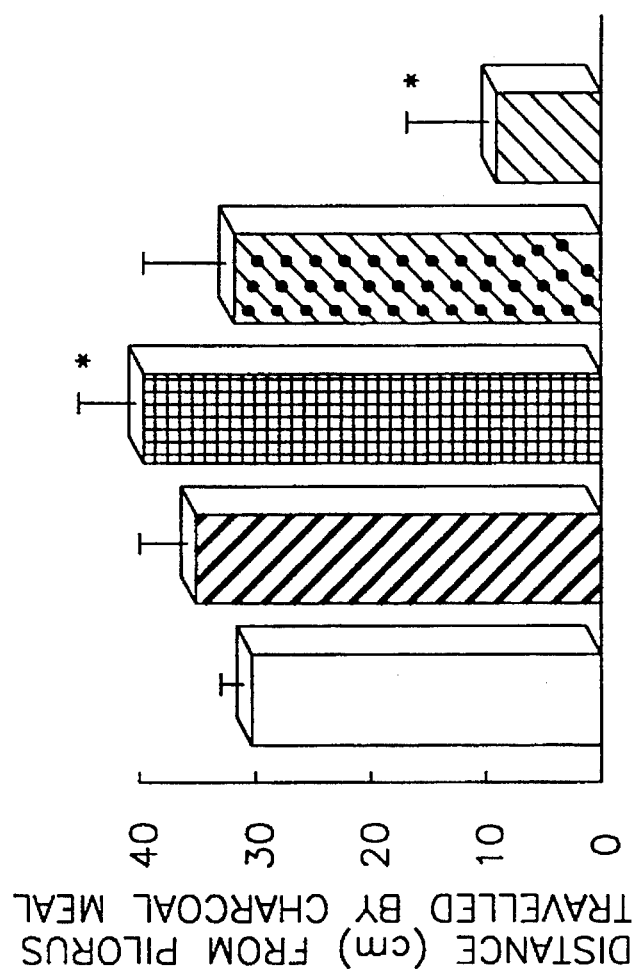
FIG. 6 shows the effect of SM-21, PG-9 and SM-32 in comparison with morphine on mouse intestinal transits.

FIG. 6 shows that the claimed compounds, unlike morphine, do not reduce the intestinal transit of a meal based on charcoal. Vertical lines gives s.e. mean. Each column represents the mean of 4–6 mice.

The meal, administered at the dose of 0.1 ml/10 g x os, cosists of a mixture of 5% carboxymethylcellulose and 20% vegetable charcoal. It was given 10 min after drugs.

Mice were sacrificed by diethylester exposure 30 min after administration.

Measurements were performed by Parolaro et al.'s technique [Eur. J. Pharmacol., 46, 329 (1977)], with minor modifications as required to test mice instead of rats. The distance that the meal covers from the pylorus is given in cm. The meal, fed per os 10 min. after drug administration (10 ml/kg), consisted of a mixture of 5% carboxymethylcellulose and 20% vegetable charcoal. Mice were sacrificed 30 min. after meal feeding. It is, therefore, clear that the claimed products do not produce, as opioids do, untoward costive effects.

Figure 7:
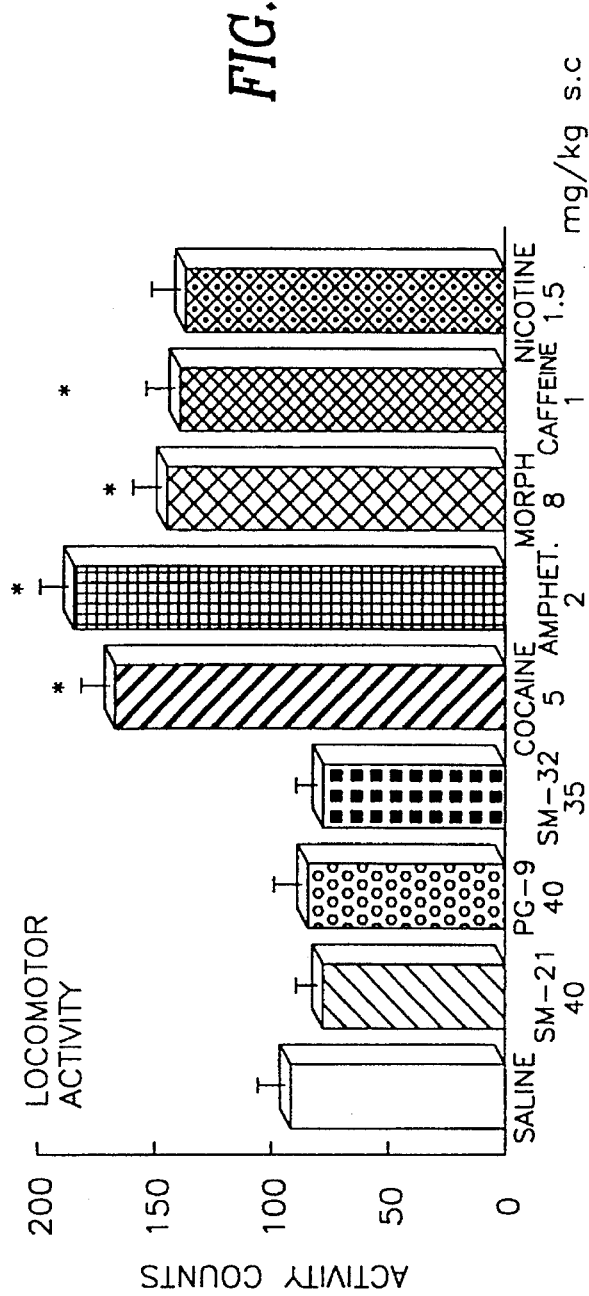
FIG. 7 and FIG. 7 bis show the effect of SM-21, PG-9 and SM-32 in comparison with Cocaine, amphetamine, morphine, caffeine and nicotine on mouse tested on hole-board.
Figure 7:
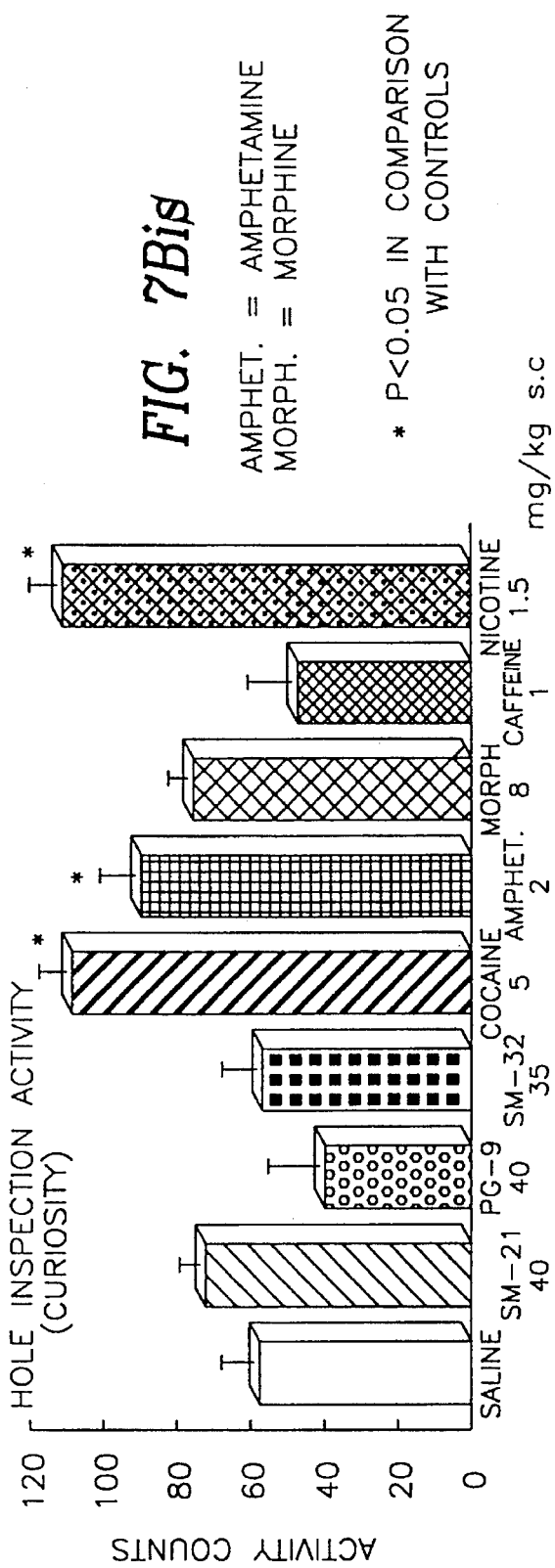

In FIGS. 7 and 7 bis vertical lines give s.e. mean. Each column represents the mean of 6–10 mice. SM-21 maleate, PG-9 maleate, SM-32 oxalate, cocaine HCl, amphetamine sulphate and caffeine were administered 15 min before test. Morphine HCl and nicotine hydrogen tartrate were administered respectively 30 min and 5 min before test.

The claimed products exert analgesic action at CNS level, but are free from the main pharmacological characteristics of addiction-producing drugs. In fact, they a) do not alter the motor activity and the "curiosity" (exploration activity) of the mice subjected to the boredboard test (as represented in the diagrams of FIG. 7 and FIG. 7 bis). As already known and as shown in FIG. 7, other drugs producing physical and/or psychic addiction. e.g. morphine. cocaine, amphetamine, caffeine, and nicotine, remarkably increase the motor activity;

b) have considerably different chemical structures from addiction-producing drugs. Also the molecular structure of cocaine, which apparently most approaches the claimed structures, is very different because of its space configuration. In fact, cocaine is a β-tropanol derivative whereas the claimed compounds are α-tropanol derivatives. Moreover, unlike the claimed compounds, cocaine activates the dopaminergic system. Conversely, the claimed compounds prevailingly act through the cholinergic system, their analgesic activity being completely antagonized by atropine (5 mg/kg i.p. ) and by hemicholinium No. 3 ( 1 μg/mouse i.c.v. ). As known, hemicholinium No. 3 inhibits choline uptake and by synthesis inhibition depletes the brain acetylcholine content. The claimed products represent a new class of nootropic and analgesic drugs acting through a mechanism of amplification of central cholinergic response.

The claimed drugs act at CNS level as proved by the following evidences:

1. They are effective even when administered directly into the cerebral ventricles at completely ineffective doses by parenteral routes.

2. The analgesia induced by said drugs is prevented by i.c.v. HC-3 pretreatment.

3. The chemical lesion of magnocellular basal nucleus prevents the onset of analgesia by the claimed products but not by other analgesic drugs (morphine and baclofen) acting through non-cholinergic mechanisms (Table 8). In fact, as known, the magnocellular basal nucleus destruction causes the degeneration of most central cholinergic system.

The mechanism of amplification of physiologically stimulated cholinergic response presumably takes place by suppression of the presynaptic inhibitory mechanisms of neuronal autoregulation.

The claimed drugs have the enormous advantage over the direct muscarinic receptors agonists that they do not produce untoward side effects, such as nausea, sialorrhoea, diarrhoea, tremors, bradycardia, etc., attributable to the massive stimulation of the cholinergic system, both central and peripheral. In fact, the direct muscarinic receptors agonists not only amplify (strengthen) a physiologically present cholinergic response, but indiscriminately activate all muscarinic receptors, independently of their being—at that moment—activated or not.

The claimed products exert a much higher nootropic and analgesic action than cholinesterase inhibitors. The latter have not to be active in the absence of physiological firing in theory, but in practice develop their analgesic and nootropic efficacy on the onset of cholinergic symptomatology.

Furthermore, the claimed products—even if administered at doses exceeding the analgesic and nootropic ones and up to toxic doses—do not bring about any symptomatology ensuing postsynaptic muscarinic receptors blockade (anticholinergic symptomatology) and do not modify the parasympathomimetic symptomalogy ensuing oxotremorine administration.

Figure 8:
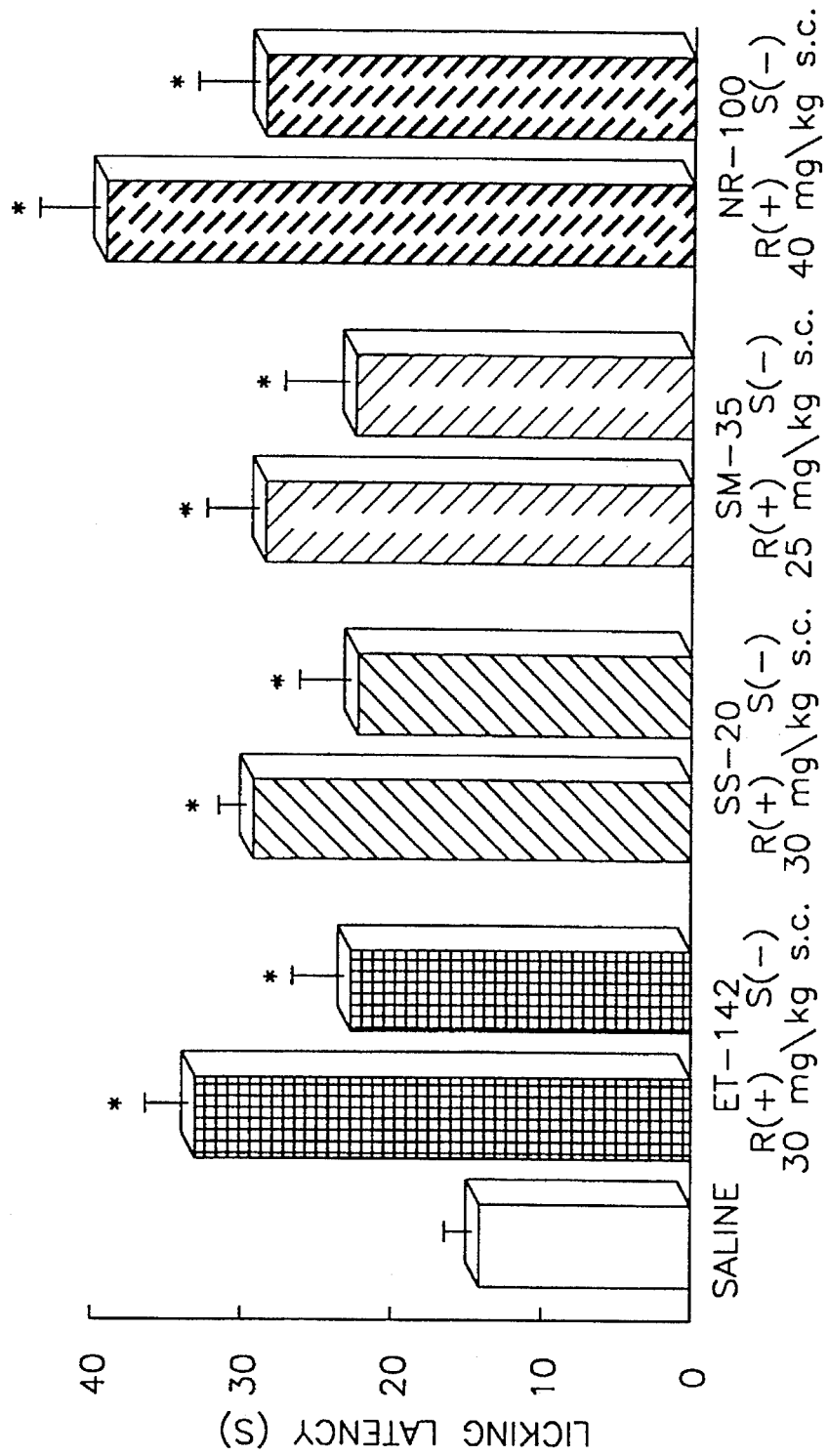
FIG. 8 shows the effect of R (+) and S(−) enantiomers of ET-142, SS-20, SM-35 and NR-100 in mouse hot-plate test (52.5° C.).

The molecular structure of all claimed compounds is chiral type: their activity, though detectd also in enantiomer S(−) , is very high in isomer R(+) . The degree of analgesic activity of the two enantiomers of the four products taken as example is illustrated in FIG. 8, in which ET-142 maleate, SS-20 maleate, SM-35 maleate and NR-100 citrate are reported.

Bars showing the same hatching represent the two enantiomers of the same molecules. Vertical lines give s.e. mean. Test was performed 30 min after treatment for all drugs except SM-35 which was tested 15 min after test. Each column represents the mean of 6–10 mice.

CLINICAL APPLICATIONS

The claimed products can treat a great number of disorders, such as for example:

senile and presenile cognitive deterioration, Alzheimer's disease, mind disorders caused by cerebral insufficiency, cognitive loss in the elderly, memory deficit in school-age young people, etc., and certain types of pain including:

surgical and dental pain, postoperative pain, posttraumatic pain, neuralgic pain (diabetic and herpetic neuropathy, trigeminal neuralgia, etc.), muscular pain (lumbago, ischialgia, etc.), neoplastic plan, obstetric-gynaecologic pain, bone and orthopaedic conditions; arthrosic and arthritic pains, adiposis dolorosa, pain due to administration of contrast media and to endoscopic tests in radiology and instrumental diagnostics, and visceralgia.

Cephalalgy and hemicrania.

WAYS OF ADMINISTRATION

The compounds under the invention are active no matter how they are administered (by the parenteral, enteral, e.g. oral or rectal, transdermic ways). Oral administration is usually preferred.

CHEMICAL STRUCTURE OF THE PRODUCTS UNDER THE INVENTION

The products under the present invention are represented by the above reported general formula (I) wherein the preferred ones are those having the following radicals:

Phenyl for Ar p.Cl and p.Br or H for $R_1$;

$CH_3$ or $C_2H_5$ for $R_2$

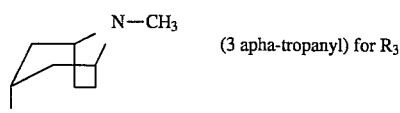

(3 apha-tropanyl) for $R_3$ none, S, O, for X
H for $R_5$
O for Y

The aforesaid compounds can be advantageously salified with pharmacologically acceptable salts.

PREPARATION PROCEDURES

A) The products where X=O, S and AF=phenyl were obtained through the following reactions:

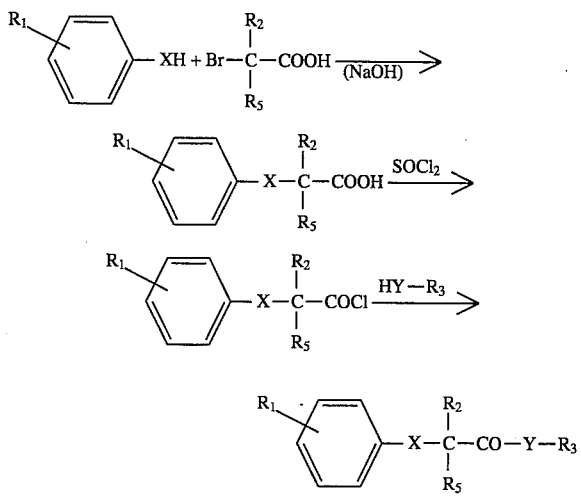

The same reactions can be applied for the case wherein Ar is different from phenyl according to the meaning pointed out for the general formula (I).

The following products are reported by way of example:

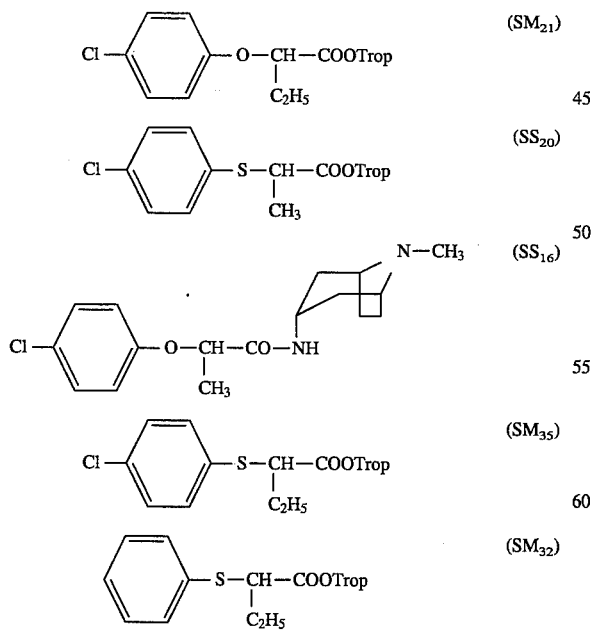

B) The products where X=NH, $NCH_3$ and Ar=phenyl were obtained through the following reactions:

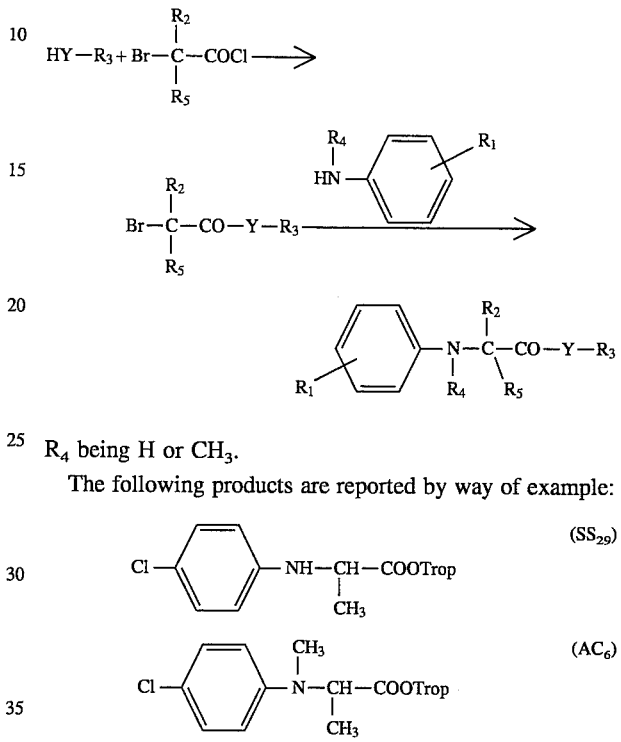

$R_4$ being H or $CH_3$.

The following products are reported by way of example:

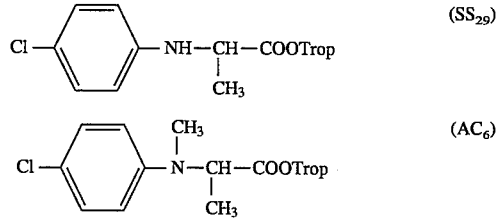

C) The products where X is not present (X=none), Ar=phenyl and $R_5$=H were obtained through the following reactions:

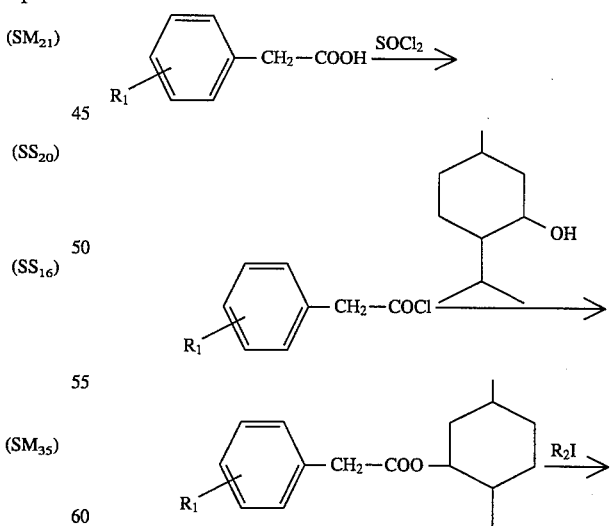

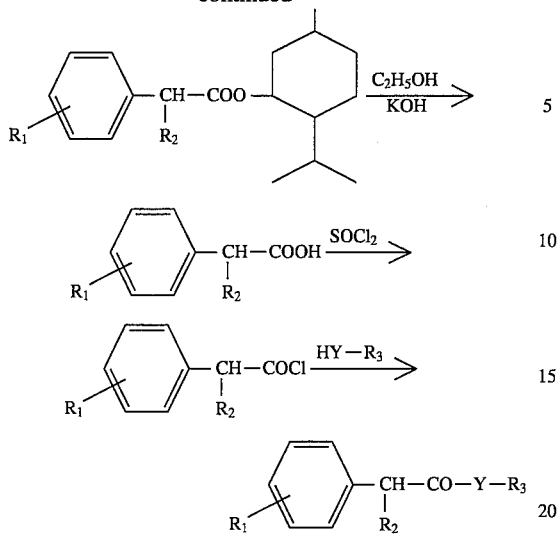

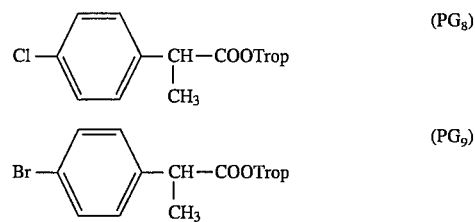

The products containing aromatic heterocyclic structure were also abtained as follows:

The above reactions—compared with the procedures already known and commonly used—give 2-aryl alkanoic acids in higher yields and of higher purity.

The same reactions can be applied for the case wherein Ar is different from phenyl according to the meaning pointed out for the general formula (I).

Alternatively, the following procedure can be applied:

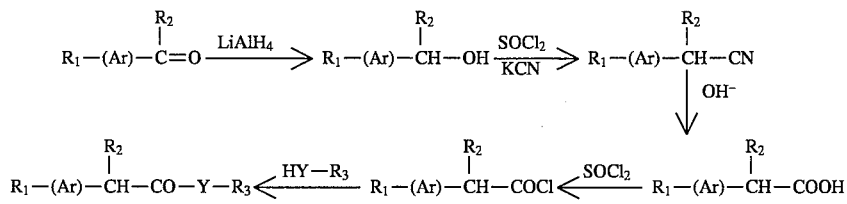

wherein the reduction with $LiAlH_4$, the chloruration of OH with $SOCl_2$, the reaction with KCN and the hydrolysis of nitrile group, occur according to conventional working conditions.

SCHEME 2

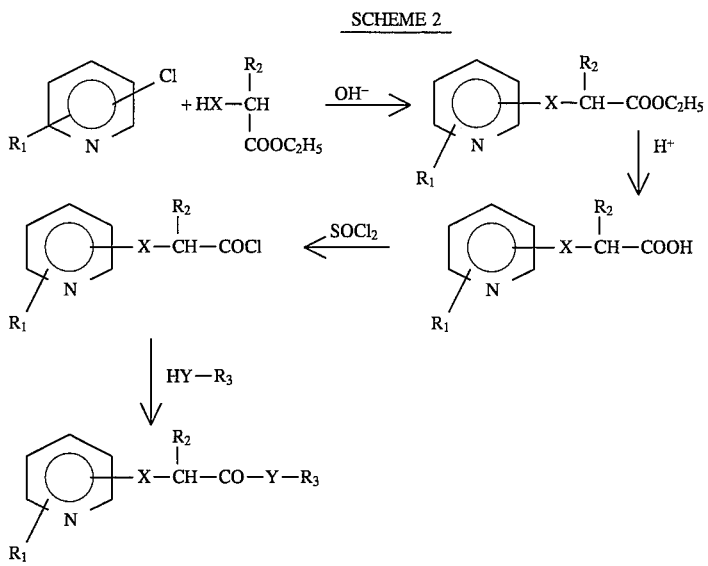

The following product is reported by way of example:

3α tropanyl 2-(5-chloropiridyn-2-oxy)butyrate ⟶

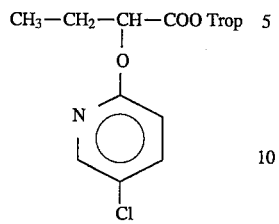

The following products are reported by way of example:

3α tropanyl 2-(4-chlorophenylethenyl)butyrate ⟶

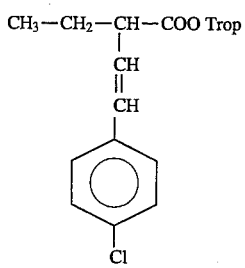

The prodcts where $$X = \phantom{x}{>}CH=CH{<}\phantom{x} \text{ or } -C\equiv C-$$

were synthetized according to the following procedure:

SCHEME 3

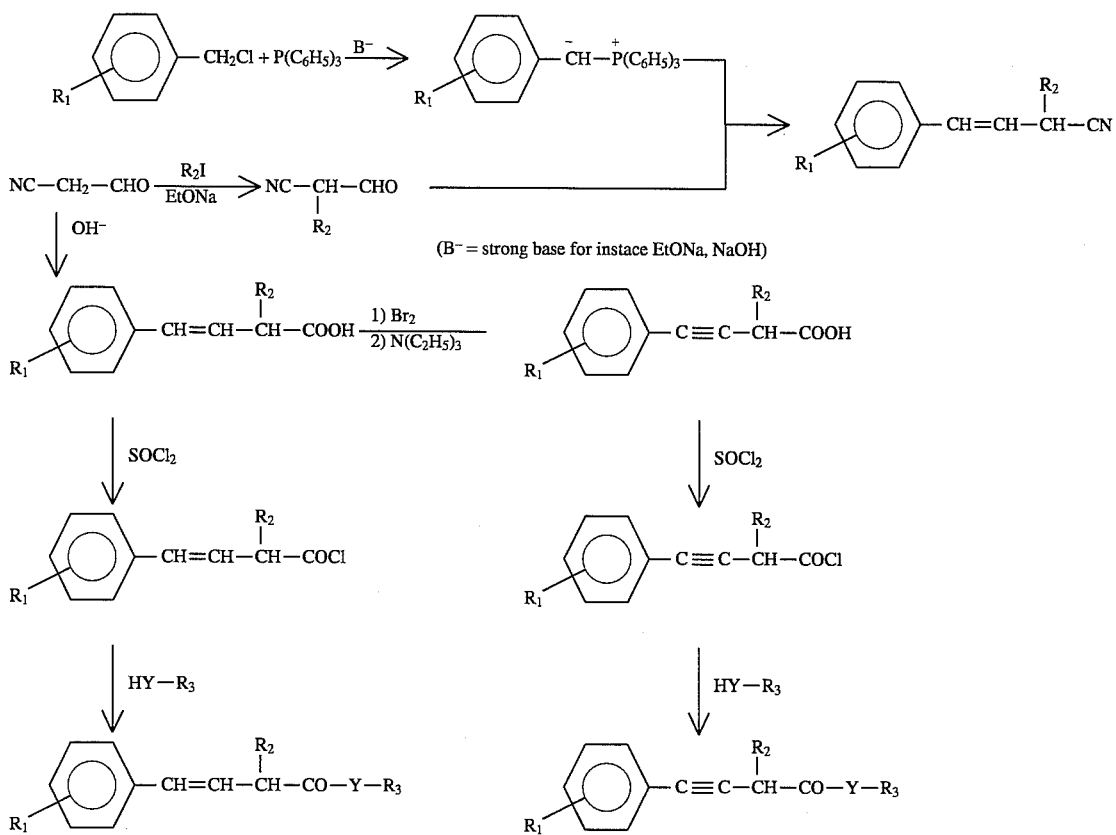

(B⁻ = strong base for instace EtONa, NaOH)

wherein the single reaction steps are carried out according to usual working conditions.

-continued

3α tropanyl 2-(4-chlorophenylethynyl)butyrate ——>

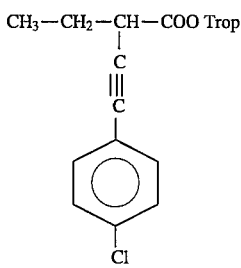

CHIRAL PRODUCTS (OPTICAL ISOMERS)

Chiral compounds are obtained from chiral acids (separated on the basis of known methods) according to the procedure adopted for the synthesis of the corresponding racemates.

The following examples are given:

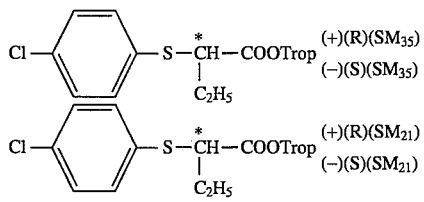

GENERAL METHOD FOR THE SYNTHESIS OF α-PHENOXY AND α-PHENYLTHIO ALKANOIC ACIDS

Several of the acids used were known; others, still unknown, were obtained as per the following general method:

NaOH pellets (0.2 mol; 8.0 g) were hot dissolved in absolute ethanol (300 ml). The solution was added with α-bromo alkanoic acid (0.1 mol) and a phenol or thiophenol compound (0.1 mol) and refluxed for 24 hours.

This procedure is always suitable for thiophenols. With phenols, instead, it is sometimes necessary to evaporate the alcohol solution to dryness, replace alcohol with anhydrous DMF (100 ml), and operate at 80° C. for 48 hours. In any case, at the reaction end, the solvent was removed under vacuum, the residue was taken up with $H_2O$ (100 ml), thoroughly acidified, and extracted with ether. The ether was then extracted with an $NaHCO_3$ saturated solution to yield, by acidification, an acid which precipitated in solid form or was extracted with ether. Yields ranged from 60 to 80%.

GENERAL METHOD FOR THE SYNTHESIS OF 2-ARYL SUBSTITUTED ALKANOIC ACIDS

Several of the acids used were known and were generally obtained from the corresponding phenylacetic acids by alkylation in α-position of the corresponding menthol esters.

By this method, higher yields of said acids were obtained and the parasite reaction bringing about dialkylation was avoided.

Substituted phenylacetic acid (0.1 mol) was hot dissolved in $SOCl_2$ (20 ml) and stirred at 60° C. for 50 min. Excess $SOCl_2$ was removed and the solution was taken up twice with cyclohexane (30 ml). The solvent was evaporated each time. The oil residue was dissolved in $CH_2Cl_2$ (50 ml) and added with menthol (0.1 mol). The mixture was maintained at 40° C. for 60 min and the solvent was eliminated. The ester residue, generally obtained in oil form, was used without any further purification in the following reaction.

Ester (0.1 mol) in toluene (30 ml) was added to $NaNH_2$ suspension (0.2 mol) in toluene (30 ml). The suspension was vigorously stirred for 10 min, cooled to 0° C., added with alkyliodide (0.2 mol), and maintained at room temperature for 40 min. The mixture was diluted with $H_2O$ and extracted with $CHCl_3$. Solvent evaporation gave an oil which was used as is in the following reaction.

Menthol ester (0.1 mol) obtained in the preceding reaction was dissolved in ethanol (30 ml), added to KOH saturated solution in ethanol (30 ml) and refluxed for 2 hours.

Acidification with 6N HCl and extraction with $CHCl_3$ gave a product which was purified by crystallization or distillation. Total yields of 60 to 80%.

GENERAL METHOD FOR THE SYNTHESIS OF α-PHENOXY AND α-PHENYLTHIO ALKANOIC ACID ESTERS OR AMIDES

Thoroughly dried α-phenoxy or α-phenylthio alkanoic acid (0.1 mol) was refluxed with $SOCl_2$ (50 ml) for 1 hr. Thionyl chloride was evaporated under vacuum and the residue was taken up with anhydrous benzene (50 ml) and evaporated to dryness.

After repeating the operation twice, the product was used as is in the following reaction.

Acyl chloride (0.1 mol) in $CH_2Cl_2$ (200 ml) was added with water-free alcohol or amine (0.1 mol) and stirred at room temperature overnight in the presence of excess anhydrous $Na_2CO_3$. The organic solution was treated with a $Na_2CO_3$ saturated solution and then with $H_2O$. The dried organic solution was evaporated to dryness generally to form an oily product, which was converted into the suitable salt. Yields ranged from 50 to 70%.

EXAMPLE 1

3α-Tropanyl 2-(p-chlorophenoxy)-butyrate (SM-21)

(Table 9 No. 8)

2-(p-Chlorophenoxybutyric)acid (3.0 g; 0.014M) [L. F. Berhenke et al., J. Am. Chem. Soc., 73, 4458, 1952] was converted into the chloride according to the general method and caused to react with 3α-tropanol (1.97 g; 0.014 mol) in $CH_2Cl_2$ (20 ml) overnight and at room temperature. The mixture treated as per the general method gave a thick oil (2 g) which was converted into the maleate. M.p.=100°–102 C. (from abs. ethanol-anhydrous ether). IR (Nujol) v=1750 $cm^{-1}$ (CO).

$^1$H—NMR ($D_2O$) δ=1.95 (t,3,—$CH_2$—$CH_3$); 2.67 (s,3, N—$CH_3$); 4.75 (t,1, O—CH—C0—); 5.04 (t,1,C0—O—CH); 6.82 (d,2,aromatic protons ); 7.21 (d,2,aromatic protons) ppm.

Analysis: $C_{18}H_{24}ClNO·C_4H_4O_4$; calcd. %: C=58.21; H=6.22; N=3.09;

found %: C=58.38; H=6.04: N=3.18.

EXAMPLE 2

3α-Tropanyl 2-(p-chlorophenylthio)propionate (SS-20)

(Table 9 No. 12)

According to the general method, 2-(p-chlorophenylthio)-propionic acid (2.0 g; 0.0093 mol) [Fawcett et al., Ann. Appl. Biol., 43,342, 1955] was converted into the chloride and caused to react with 3α-tropanol (1.3 g; 0.0093 mol) in $CH_2Cl_2$ (20 ml) at room temperature. The mixture treated according to the general method gave a thick oil (2.53 g) which was converted into the maleate. M.p.=120°–122° C. (from abs. ethanol). IR (Nujol) ν=1730 $cm^{-1}$ (CO).

$^1$H-NMR ($CDCl_3$) δ=1.48 (d,3,—S—CH—$CH_3$); 2.72 (s,3,N—$CH_3$); 5.08 (t,1,CO—O—CH); 7.30 ( m,4,aromatic protons) ppm.

Analysis: $C_{17}H_{22}ClNO_2S \cdot C_4H_4O_4$; calcd. %: C=55.32; H=5.75;

N=3.07; found %: C=55.48; H=5.53; N=3.21

EXAMPLE 3

3α-Tropanyl 2-(p-chlorophenoxy)-isobutyrate (SM-25)

Commercially available clofibric acid (4.0 g; 0.018 mol) was converted into the chloride and caused to react with 3α-tropanol (2.54 g; 0.018 mol) in $CH_2Cl_2$ (40 ml) according to the described general method. The mixture treatment gave an oily product (5.2 g) which was converted into the oxalate. M.p.=153°–155° C. (from abs. ethanol). IR (Nujol) ν=1740 $cm^{-1}$ (CO).

$^1$H—NMR ($D_2O$) δ=1.58 (s,6,—$C(CH_3)_2$; 2.69 (s,3,N—$CH_3$); 5.13 (t,1,CO—O—CH); 6.88 (d,2,aromatic protons); 7.30 (d,2,aromatic protons) ppm.

Analysis: $C_{18}H_{24}ClNO_3 \cdot C_2H_4O_4$; calcd. %: C=56.14; H=6.12;

N=3.27; found %: C=55.97; H=6.03; N=3.40.

EXAMPLE 4

N-(3α-tropanyl)-2-(p-chlorophenoxy)-propionamide (5) SS-16

(Table 9 No. 23)

2-(p-Chlorophenoxy)-propionic acid (2 g; 0.01 mol) was converted into the chloride and caused to react with 3α-aminopropane (1.4 g; 0.01 mol) in $CH_2Cl_2$ (20 ml). Operation according to the above procedure gave a thick oil (3.1 g) which must be purified by silica gel chromatography (eluent $CHCl_3$=340, abs. EtOH=60, petroleum ether=65, conc. $NH_4OH$=8) to yield a base (1.2 g) which was converted into the hydrochlorate. M.p. 65° C. (dec.) from abs. ethanol. IR (Nujol) ν=1640 $cm^{-1}$ (CO).

$^1$H—NMR ($D_2O$) δ=1.98 (d,3,—O—CH—$CH_3$); 2.21 (s,3,N—$CH_3$); 4.05 (q,1,CO—NH—CH); 4.59 (q,1,O—CH—$CH_3$); 6.83 (d,2,aromatic protons); 7.27 (d,2,aromatic protons) ppm.

Analysis: $C_{17}H_{32}ClN_2O_2 \cdot HCl$; calcd. %: C=56.83; H=6.73; N=7.8;

found %: C=57.03; H=6.81; N=7.63.

EXAMPLE 5

3α-Tropanyl 2-(p-chlorophenylthio)-butyrate (SM-35)

(Table 9 No. 17)

2-(p-Chlorophenylthio)-butyric acid (3.8 g; 0.0165 mol) [C. H. Fawcett, Ann. Appl. Biol., 43, 342, 1955] was converted into the chloride and caused to react with 3α-tropanol (2.33 g; 0.0165 mol) in $CH_2Cl_2$ (40 ml) according to the general method. An oily product was obtained (4.2 g) which was converted into the oxalate. M.p. 130°–133° C. (from abs. ethanol/anhydrous ether). IR (Nujol) ν=1735 $cm^{-1}$ (CO).

$^1$H—NMR ($D_2O$) δ=0.98 (t,3,$CH_2$—$CH_3$); 2.67 (s,3,N—$CH_3$); 4.93 (t,CO—O—CH); 7.32 (d,2,aromatic protons); 7.44 (d,2,aromatic protons) ppm.

Analysis: $C_{18}H_{24}ClNO_2S \cdot C_2H_2O_4$; calcd. %: C=63.22; H=6.90;

N=3.69; found %: C=63.47; H=6.67; N=3.50.

EXAMPLE 6

3α-Tropanyl 2-(phenylthio)-butyrate (SM-32)

(Table 9 No. 16)

The procedure was as per Example 5 using thiophenol instead of 4-chlorophenol. The oxalate crystallized from ethanol and melted at 143°–145° C. IR (Nujol) ν=1730 $cm^{-1}$ (CO).

$^1$H—NMR ($D_2O$) δ=0.98 (t,3,$CH_2$—$CH_3$); 2.65 (s,3,N—$CH_3$); 3.82 (t,1,S—CH—$CH_2$—); 4.92 (t,CO—O—CH); 7.15 (m,3,aromatic protons);

7.48 (m,2,aromatic protons) ppm.

Analysis: $C_{18}H_{25}NO_2S \cdot C_2H_2O_4$; calcd. %: C=58.65; H=6.66; N=3.42;

found %: C=58.77; H=6.46; N:3.61.

EXAMPLE 7

3α-Tropanyl 2-(p-chlorophenylamino)-propionate ($AC_5$)

(Table 9 No. 20)

2-Bromopropionic acid (6.5 g; 0.042 mol) was converted into the chloride by reaction with $SOCl_2$ (6.2 ml; 0.084 mol) at 50° C. The product was isolated by Fractional distillation (b.p. 120°–125° C.). Acid chloride (0.68 g; 0.0039 mol ) was added to tropanol hydrochlorate (0.7 g; 0.0039 mol ) in $CHCl_3$ (20 ml ). The solution was maintained at 50° C. For 8 hours, then added with distilled aniline (0.73 g; 0.0078 mol) in $CHCl_3$ (10 ml), refluxed For 6 hours and, after cooling, washed with an $Na_2CO_3$ saturated solution, and dried. Evaporation to dryness gave an oily product (1.2 g) , which was taken up with anhydrous ether, bubbled with gaseous HCl. The hydrochlorate precipitate was recrystallized From abs. ethanol. Yield 0.72 g. M.p. 218°–220° C.

IR (Nujol) C=1740 $cm^{-1}$ (CO); 3430 $cm^{-1}$ (NH).

$^1$H—NMR ($D_2O$) ε=1.63 (d,3,CH—$CH_3$); 2.78 (s,3,N—$CH_3$); 4.62 (q,1,NH—CH$CH_3$); 5.18 (t,1,CO—O—CH); 7.30–7.60 (m,5,aromatic protons) ppm. Analysis: $C_{17}H_{23}ClO_2N_2 \cdot HCl$; calcd. %: C=56.82; H=6.75; N=7.80; Cl=19.73; Found %: C=57.04; H=6.77; N=7.83; Cl=19.79.

EXAMPLE 8

3α-Tropanyl 2-[N-methyl-N(p-chlorophenyl)amino]-propionate (AC-6)

(Table 9 No. 21)

Procedure as per Example 7 using N-methylaniline. The maleate obtained from the final product was recrystallized from ethanol. M.p. 118°–120° C. (after drying under vacuum). IR (Nujol) of the free base ν=1735 $cm^{-1}$(CO).

$^1$H—NMR ($D_2O$) (of maleate) δ=1.50 (d,3,CH—$CH_3$); 2.67 (s,3,N—$CH_3$); 2.85 (s,3,N—$CH_3$); 4.48 (q,1,CH—$CH_3$); 5.12 (t,1,CO—O—CH—);

6.71 (d,2,aromatic protons); 7.18 (d,2,aromatic protons) ppm.

Analysis: $C_{18}H_{25}ClO_2N_2 \cdot C_4H_4O_4$; calcd, %: C=58.41; H=6.42;

N=6.19; Cl=7.83; found %: C=58.29; H=6 53; N=6.24; Cl=7.61.

EXAMPLE 9

3α-Tropanyl 2-(p-chlorophenyl)-propionate (PG-8)

(Table 9 No. 25)

2-(p-Chlorophenyl)-propionic acid (0.4 g; 0.0022 mol) [F. Nardel et al., Chem. Bet., 87, 217, 1954] was treated with $SOCl_2$ (4 ml) an 60° C. for 2 hrs. Excess thionyl chloride was eliminated and the mixture was repeatedly washed with cyclohexane. The oil residue was added with $CH_2CL_2$ (5 ml) and 3α-tropanol (0.5 g; 0.0044 mol) and the mixture was maintained at room temperature overnight. The organic solvent was eliminated, the residue was taken up with water, alkalinized with NaOH, and extracted with ether to yield 0.5 g of raw product, which was purified from excess 3α-tropanol by silica gel chromatography (eluent as per Example 4). An oily product (0.35 g) was obtained and converted into the maleate. M.p. 137°–139° C. from abs. ethanol. IR (Nujol) v=1740 $cm^{-1}$ (CO).

$^1$H—NMR ($CDCl_3$) δ=1.77 (d,3,CH—$CH_3$); 3.65 (q,1, N—CH—$CH_3$); 5.05 (t,1,CO—O—CH); 7.10–7.40 (m,4, aromatic protons) ppm. Analysis:

$C_{17}H_{22}ClNO_2 \cdot C_4H_4O_4$; calcd. %: C=59.50; H=6.18; N=3.30; found %:

C=59.84; H=6.30; N=2.99.

EXAMPLE 10

3α-Tropanyl 2-(p-bromophenyl)-propionate (PG-9)

(Table 9 No. 26)

2-(p-Bromophenyl)-propionic acid (0.3 g; 0.0013 mol) [D. C. Abbott et al., J. Chem. Soc., 2934, 1952] was caused to react with 3α-tropanol (0.55 g; 0.0039 mol) according to the procedure described in Example 9. The raw product obtained (0.55 g) was purified by silica gel chromatography (eluent as per Example 4).

An oil (0.3 g) was obtained and converted into the maleate.

M.p. 148°–150° C. from abs. ethanol. IR (Nujol) v=1730 $cm^{-1}$(CO).

$^1$H—NMR ($CDCl_3$) δ=1.50 (d,3,CH—$CH_3$); 2.65 (s,3, N—$CH_3$); 3.68 (q,1,CH—$CH_3$); 5.05 (t,1,CO—O—CH); 7.10–7.50 (m,4,aromatic protons) ppm. Analysis: $C_{17}H_{22}BrNO_2 \cdot C_4H_4O_4$; calcd. ,%: C=53.85; H=5.60: N=2.99; found %: C=54.06: H=5.45; N=2.78.

EXAMPLE 11

N-Ethyl-3α-nortropanyl 2-(p-chlopophenoxy)butyrate (GC-11) 2-(p-Chlorophenoxy)butyric acid (3.0 g; 0.014 mol) was converted into the chloride according to the described general method and caused to react with N-ethyl-3α-nortropanol (1.97 g; 0.014 mol) [A. Berthold et al., Arzneim.-Forsch., 17, 719 (1967)] in $CH_2Cl_2$ (20 ml) overnight at room temperature.

Operation according to the above procedure gave a thick oil which was converted into the oxalate. M.p. 150°–151° C. from abs. ethanol/anhydrous ether. IR (Nujol) 1755 $cm^{-1}$ (CO).

$^1$HNMR ($CDCl_3$) δ=1.1 (t,3,$CH_2$—$CH_2$—$CH_3$); 1.3 (t,3, N—$CH_2$—$CH_3$);

4.58 (t,1,O—CH—CO); 5.58 (s,1,CO—O—CH); 6.80 (d,2,aromatic protons); 7–25 (d,2,aromatic protons) ppm.

Analysis: $C_{21}H_{28}ClNO_7$; calcd. %: C=57.07; H=6.40, N=3.17; found %: C=57.30; H=6.22; N=3.15.

EXAMPLE 12

3α-Tropanyl 2-(β-naphthoxy)propionate (AC-19)

2-(β-Naphthoxy)propionic acid (0.01 mol) [C. A. Bischoff et al., B. 1900, 33, 1386] was converted into the chloride according to the described general method and caused to react with 3α-tropanol (0.01 mol) in $CH_2Cl_2$ (20 ml) overnight at room temperature. The mixture treated according to the general method gave a thick oil which was converted into the maleate.

Yield 95%. M.p. 115°–117° C. from abs. ethanol/anhydrous ether.

IR (Nujol) 1750 $cm^{-1}$ (CO).

$^1$HNMR ($CDCl_3$) δ=1.25 (d,3,—O—CH—$CH_3$); 2.63 (s,3,N—$CH_3$); 4.98 (q,1,O—CH—$CH_3$); 5.18 (t,1,CO—O—CH); 7.00–8.00 (m,7,aromatic protons) ppm.

Analysis: $C_{25}H_{29}ClNaO_7$; calcd. %: C=65.91; H=6.43, N=3.08; found %: C=65.73; H=6.55; N=2.96.

EXAMPLE 13

(R)(+) and (S)(–) 3α-Tropanyl 2-(p-chlorophenylthio)butyrate

[(R)(+) SM-35 and (S)(–) SM-35]

(Table 10 Nos. 48 and 49)

(R)(+) 2-(p-Chlorophenylthio)butyric acid (0.01 mol) [V. Tortorella, private communication] was converted into the chloride with $SOCl_2$, according to the procedure described for the racemic product. The raw oil obtained was dissolved in $CHCl_3$ (30 ml). The solution was added dropwise with tropanol hydrochlorate (0.02 mol ) in $CHCl_3$ (50 ml ). The mixture obtained was refluxed for 20 hours, cooled, washed with a 10% $Na_2CO_3$ solution, and dried. Solvent evaporation yielded an oil which was converted into the maleate. Likewise, the other enantiomer was obtained from the corresponding (S)(–) acid. The two products showed identical spectroscopic data and the following characteristics:

(R)(+) SM-35: m.p. 74°–77° C. (from ethyl acetate/ether); $[α]^D$ 20=+85.2 (MeOH)

(S)(–) SM-35: m.p. 74°–77° C. (from ethyl acetate/ether); $[α]^D$ 20 =–87.6 (MeOH)

EXAMPLE 14

(R)(+) and (S)(–) 3α-Tropanyl 2-(p-chlorophenoxy)butyrate

[(R)(+) SM-21 and (S)(–) SM-21]

(Table 10 Nos. 52 and 53)

(R)(+) 2-(p-Chlorophenoxy)butyric acid and its enantiomer

[Sjorberg B., Ark. Kemi, 15, 451 (1960); G. Bettoni et al., J. Med. Chem., 30, 1967 (1987)] were treated according to the procedure described in Example 11 to give the two enantiomers as maleares having the following characteristics:

(+)(R) SM-21: m.p. 83°–85° C. (from abs. ethanol/ether); $[α]^D$ 20=+48.1 (MeOH)

(S)(–) SM-21: m.p. 83°–85° C. (from abs. ethanol/ether); $[α]D$ 20=–49.4 (MeOH).

The two products showed identical spectroscopic data corresponding to those of the racemate.

Table 9 lists the claimed products of formula (I), which were examined for the determination of their analgesic activity.

Table 10 lists some enantiomers of the products under the invention.

Examples of formulations for parenteral administration containing active ingredients SM-21, SM-32, and PG-9

(* stands for free bases)

1) One 2 ml vial for i.m. injection contains

| active ingredient | 25 mg | 100 mg | 350 mg* |
|---|---|---|---|
| sodium chloride | 18 mg | 27 mg | 36 mg |
| buffer | q.s. | q.s. | q.s. |
| water for injection | q.s. | q.s. | q.s. |

2) One syringe-vial for s.c. injection contains

| active ingredient | 25 mg | 50 mg | 75 mg* |
|---|---|---|---|
| water for injection | q.s. | q.s. | q.s. |
|  | 0.3 ml vial | 0.5 ml vial | 0.6 ml |

3) One 5 ml vial for i.v. injection contains

| active ingredient | 25 mg | 100 mg | 350 mg* |
|---|---|---|---|
| water for injection | q.s. | q.s. | q.s. |

4) One bottle of freeze-dried powder for i.m. injection to be dissolved in a solvent immediately prior to administration contains

| active ingredient | 25 mg | 100 mg | 350 mg* |
|---|---|---|---|
| mannitol | 100 mg | 150 mg | 200 mg |
| solvent: |  |  |  |
| buffer | q.s. | q.s. | q.s. |
| water for injection | q.s. | q.s. | q.s. |
|  | 2 ml vial | 3 ml vial | 4 ml vial |

5) One 5 ml bottle of freeze-dried powder for i.v. injection to be dissolved in a solvent immediately prior to administration contains:

| active ingredient | 25 mg | 100 mg | 350 mg* |
|---|---|---|---|
| solvent: |  |  |  |
| water for injection | q.s. | q.s. | q.s. |

Examples of formulations for oral administration containing active ingredients SM-21, SM-32, and PG-9

(* stands for free bases)

1) One hard gelatin capsule enclosing enteric granules contains

|  | mg | mg |
|---|---|---|
| active ingredient | 300 | 500 * |
| lactose | 300 | 200 |
| talc | 10 | 20 |
| magnesium stearate | 5 | 7 |
| polyvinylpyrrolidone | 10 | 15 |
| starch | 30 | 50 |

2) One tablet contains:

|  | mg | mg | mg |
|---|---|---|---|
| active ingredient | 300 | 500 | 1000 * |
| microcrystalline cellulose | 30 | 40 | 100 |
| lactose | 100 | 120 | 300 |
| talc | 10 | 10 | 30 |
| magnesium stearate | 5 | 7 | 10 |
| polyvinylpyrrolidone | 10 | 15 | 30 |
| starch | 10 | 20 | 40 |

3) One controlled release tablet contains

|  | mg | mg | mg |
|---|---|---|---|
| active ingredient | 300 | 500 | 1000 * |
| hydroxypropyl methylcellulose | 50 | 70 | 140 |
| lactose | 100 | 120 | 300 |
| talc | 10 | 15 | 30 |
| magnesium stearate | 4 | 7 | 10 |
| polyvinylpyrrolidone | 10 | 15 | 30 |

4) One enteric coated tablet contains

|  | mg | mg | mg |
|---|---|---|---|
| active ingredient | 300 | 500 | 1000 * |
| microcrystalline cellulose | 30 | 40 | 100 |
| lactose | 100 | 120 | 300 |
| talc | 10 | 10 | 30 |
| magnesium stearate | 5 | 7 | 10 |
| polyvinylpyrrolidone | 10 | 15 | 30 |
| starch | 10 | 20 | 40 |
| methacrylic acid copolymer | 30 | 50 | 100 |

5) One hard gelatin capsule enclosing enteric coated granules contains

|  | mg |
|---|---|
| active ingredient | 300 * |
| saccharose | 80 |
| starch | 30 |
| polyvinylpyrrolidone | 15 |
| methacrylic acid copolymer | 30 |

6) One soft gelatin capsule contains

|  | mg |
|---|---|
| active ingredient | 300 * |
| polyethylene glycol mixture | 100 |
| glycerol | 30 |
| gelatin | 80 |
| preservatives and colouring agents | q.s. |

7) Drops fop oral administration contain

| active ingredient | 3000 mg * |
|---|---|
| purified water | 20 ml |
| flavour | q.s. |
| sweetener | q.s. |
| preservative | q.s. |

8) One soft gelatin enteric coated capsule contains

|  | mg |
|---|---|
| active ingredient | 300 * |
| polyethylene glycol mixture | 100 |
| glycerol | 30 |
| gelatin | 80 |
| preservative | q.s. |
| colouring agent | q.s. |
| methacrylic acid copolymer | 30 |

Some examples of formulations containing active ingredients SM-21, SM-32, PG-9

(* stands for free bases)

1) One 2000 mg suppository for rectal administration contains

| active ingredient | 50 mg | 100 mg | 150 mg* |
|---|---|---|---|
| semisynthetic triglyceride mixture | q.s. | q.s. | q.s. |

2) One capsule for rectal administration contains

|  | mg | mg | mg |
|---|---|---|---|
| active ingredient | 50 | 100 | 150 * |
| polyethylene glycol mixture | 300 | 600 | 900 |
| gelatin | 200 | 250 | 300 |
| glycerol | 80 | 100 | 120 |
| preservatives and colouring agents | q.s. | q.s. | q.s. |

Some examples of Formulations containing active ingredients SM-21, SM-32, and PG-9

Controlled release preparation for transdermic use Drug-dispensing plaster to be applied to the skin

|  | mg | mg | mg |
|---|---|---|---|
| active ingredient | 100 | 200 | 300 * |
| purified water | 20 | 40 | 60 |
| polycarboxymethylene | 10 | 20 | 30 |
| n-methylpyrralidone | 10 | 20 | 30 |
| polyoxyethylene glyceride mixture | 5 | 10 | 15 |

TABLE 1

| | | ROTA-ROD (16 r.p.m.) performance (Number of falls in 30 s.) | | | |
|---|---|---|---|---|---|
| Treatment | | Before | After treatment | | Highest dose (mg/kg) ineffective |
| mg/kg | | treatment | 15 min | 30 min | 45 min | on rota-rod* |
| Saline s.c.(x) | | 2.2 ± 0.3 | 1.8 ± 0.3 | 1.4 ± 0.2 | 0.8 ± 0.2 | 8.2 |
| Morph HCl | 5 | 1.8 ± 0.4 | 1.7 ± 0.4 | 0.6 ± 0.2 | 0.8 ± 0.3 | |
| s.c. | 7 | 2.5 ± 0.6 | 2.0 ± 0.4 | 1.5 ± 0.4 | 1.0 ± 0.2 | |
| | 10 | 1.6 ± 0.3 | 1.6 ± 0.4 | 1.3 ± 0.3 | 0.5 ± 0.2 | |
| | 20 | 2.4 ± 0.4 | 2.8 ± 0.5 | 3.1 ± 0.3 | 2.7 ± 0.3 | |
| DFD | 25 | 2.2 ± 0.5 | 2.0 ± 0.5 | 1.0 ± 0.3 | 1.4 ± 0.4 | 20.5 |
| s.c. | 30 | 2.5 ± 0.3 | 2.1 ± 0.4 | 1.5 ± 0.3 | 1.5 ± 0.4 | |
| | 40 | 2.8 ± 0.5 | 4.3 ± 0.4 | 3.1 ± 0.4 | 2.3 ± 0.4 | |
| Clom. HCl | 25 | 2.9 ± 0.5 | 2.4 ± 0.5 | 2.1 ± 0.6 | 2.1 ± 0.6 | 20.2 |
| s.c. | 45 | 2.4 ± 0.2 | 2.8 ± 0.4 | 3.6 ± 0.4 | 3.5 ± 0.6 | |
| | 50 | 1.9 ± 0.4 | 1.8 ± 0.4 | 1.8 ± 0.4 | 1.5 ± 0.4 | |
| | 60 | 1.2 ± 0.3 | 1.5 ± 0.4 | 2.6 ± 0.3 | 3.1 ± 0.5 | |
| Ketor. Tr. | 200 | 1.6 ± 0.3 | 1.7 ± 0.3 | 0.5 ± 0.2 | 0.5 ± 0.2 | 175 |
| i.p. | 250 | 1.2 ± 0.2 | 1.5 ± 0.2 | 1.4 ± 0.4 | 1.2 ± 0.3 | |
| | 300 | 1.8 ± 0.5 | 2.1 ± 0.4 | 1.7 ± 0.4 | 1.5 ± 0.4 | |
| | 350 | 2.0 ± 0.4 | 2.3 ± 0.4 | 2.1 ± 0.5 | 1.7 ± 0.5 | |
| | 400 | 2.2 ± 0.5 | 3.3 ± 0.5 | 3.8 ± 0.6 | 3.1 ± 0.6 | |
| | 473 | 1.2 ± 0.3 | 3.6 ± 0.6 | 2.6 ± 0.7 | 2.4 ± 0.5 | |
| SM-21 mal. | 30 | 2.8 ± 0.2 | 1.9 ± 0.3 | 1.5 ± 0.5 | 1.2 ± 0.5 | 38.9 |
| s.c. | 40 | 2.2 ± 0.4 | 1.6 ± 0.6 | 1.2 ± 0.4 | 1.2 ± 0.4 | |
| | 50 | 1.6 ± 0.6 | 2.2 ± 0.4 | 2.6 ± 0.5 | 2.4 ± 0.5 | |
| | 60 | 1.7 ± 0.4 | 3.5 ± 0.5 | 4.3 ± 0.4 | 4.4 ± 0.6 | |
| PG-9 mal. | 40 | 1.8 ± 0.6 | 1.2 ± 0.5 | 0.8 ± 0.4 | 1.3 ± 0.5 | 43.5 |
| s.c. | 45 | 3.1 ± 0.6 | 2.4 ± 0.8 | 1.3 ± 0.5 | 0.8 ± 0.4 | |
| | 50 | 2.2 ± 0.4 | 2.2 ± 0.6 | 2.7 ± 0.6 | 2.8 ± 0.4 | |
| SM-32 oxa. | 40 | 1.6 ± 0.5 | 1.2 ± 0.6 | 1.4 ± 0.3 | 1.2 ± 0.4 | 37.8 |
| s.c. | 45 | 2.5 ± 0.4 | 2.0 ± 0.3 | 2.3 ± 0.3 | 2.0 ± 0.5 | |
| | 50 | 1.8 ± 0.4 | 1.8 ± 0.4 | 2.6 ± 0.6 | 2.6 ± 0.5 | |

Effect of various analgesic drugs in mouse rota-rod test performed according to the method described by Vaught et al. Neuropharmacology 24, (3), 211–216, 1985. To be noted that repetition of the test session every 15 min four times induces a progressively slight decrease in the number of falls in saline-treated mice. Therefore the lack of variation, or the increase in the number of falls following treatment indicates an impairment of mice psycho- motor activity. Each value represents the mean of 10 mice with the exception of -(x)- where n = 60.
Morph. = Morphine DFD = Diphenhydramine; Clom. = Clomipramine Ketor. Tr. = Ketorolac Trometamine; mal. = maleate; oxa. = oxalate
* For each drug the highest ineffective dose was obtained as follows:
A) calculation of avareges of the differences between falls observed at 15, 30, and 45 min after treatments and falls observed before treatment.
B) Estimation of line equation of each drug was calculated with "statgraphics" regression analysis.
C) The highest ineffective dose for each drug is represented by the interception point between the line of each drug and the line of saline.

TABLE 2

| Treatment | Before treatment | HOT-PLATE (52.5° C.) latency (s) After treatment | | |
|---|---|---|---|---|
| | | 15 min | 30 min | 45 min |
| Saline 10 ml/kg i.p. | 14.4 ± 1.5 (5) | 15.6 ± 1.7 (5) | 14.0 ± 1.6 (5) | 15.2 ± 1.5 (5) |
| Saline 10 ml/kg s.c. | 14.4 ± 0.5 (20) | 14.6 ± 0.7 (20) | 15.4 ± 0.8 (20) | 13.2 ± 0.7 (20) |
| Morphine HCl 8 mg/kg i.p. | 13.7 ± 1.1 (8) | 22.7 ± 1.8^ (8) | 35.6 ± 2.0* (8) | 31.8 ± 1.9* (8) |
| Morphine HCl 8 mg/kg s.c. | 14.5 ± 1.2 (11) | 24.1 ± 1.3^ (11) | 37.1 ± 1.9* (11) | 35.2 ± 1.6* (11) |
| Diphenhydramine 20 mg/kg i.p. | 13.8 ± 0.7 (10) | 21.6 ± 2.5^ (10) | 17.7 ± 1.6 (10) | 17.1 ± 1.8 (10) |
| Diphenhydramine 20 mg/kg s.c. | 13.7 ± 0.8 (10) | 23.6 ± 2.6^ (10) | 18.0 ± 1.4 (10) | 18.7 ± 2.1 (10) |
| Clomipr. HCl 20 mg/kg i.p. | 14.2 ± 0.7 (10) | 24.8 ± 2.8* (10) | 25.2 ± 2.2* (10) | 23.2 ± 2.1^ (10) |
| Clomipr. HCl 20 mg/kg s.c. | 15.0 ± 0.8 (10) | 17.4 ± 1.1 (10) | 19.3 ± 0.9^ (10) | 16.5 ± 0.8 (10) |
| Ketorol. trom. 175 mg/kg i.p. | 14.0 ± 0.9 (10) | 26.5 ± 3.4* (10) | 19.6 ± 1.4^ (10) | 17.7 ± 1.5 (10) |
| Ketorol. trom. 175 mg/kg s.c. | 13.7 ± 0.6 (10) | 16.3 ± 1.1 (10) | 15.0 ± 1.2 (10) | 15.1 ± 1.6 (10) |
| SM-21 maleate 40 mg/kg i.p. | 14.4 ± 0.9 (8) | 36.7 ± 2.1* (8) | 32.0 ± 2.2* (8) | 25.9 ± 2.7* (8) |
| SM-21 maleate 40 mg/kg s.c. | 14.8 ± 0.8 (16) | 38.9 ± 2.9* (16) | 31.3 ± 2.5* (16) | 29.4 ± 3.3* (16) |
| PG-9 maleate 40 mg/kg i.p. | 13.8 ± 0.8 (10) | 42.5 ± 2.5* (10) | 39.7 ± 2.1* (10) | 26.7 ± 3.5* (10) |
| PG-9 maleate 40 mg/kg s.c. | 15.3 ± 1.8 (18) | 39.3 ± 3.4* (18) | 35.1 ± 2.8* (18) | 33.3 ± 2.6* (18) |
| SM-32 oxalate 35 mg/kg i.p. | 16.4 ± 0.9 (10) | 35.5 ± 3.0* (10) | 33.5 ± 2.6* (10) | 24.4 ± 1.9* (10) |
| SM-32 oxalate 35 mg/kg s.c. | 14.5 ± 0.8 (10) | 38.7 ± 3.5* (10) | 36.4 ± 3.2* (10) | 25.7 ± 2.9 (10) |

Effect of SM-21, PG-9 and SM-32 in mouse hot-plate test in comparison with four principal reference analgesic drugs. The test was performed at the highest dose ineffective on rota-rod test as shown in Table 1. *P < 0.01; ^P < 0.05 respect to saline controls. The number of mice is in parentheses. Clomip. = Clomipramine; Ketorol. trom. = Ketorolac trometamine.

TABLE 3

| Treatment | Efficacy as analgesic (Morphine = 100) | | ED50 | | DL50 | | |
|---|---|---|---|---|---|---|---|
| | M.E. | AUC | (mg/kg) | (µmol/kg) | (mg/kg) | | (µmol/kg) |
| Morphine HCl s.c. | 100 | 100 | 4.4 | 13.6 | 531 | s.c. | 1650 |
| Diphenhydramine s.c. | 43 | 28 | 12.3 | 48.1 | 127 | s.c. | 497 |
| Clomipramine HCl s.c. | 19 | 17 | 13.6 | 38.7 | 44 | i.v. | 125 |
| Ketorolac Trometamine i.p. | 55 | 46 | 125 | 332 | 473 | i.p. | 1257 |
| SM-21 Maleate s.c. | 111 | 111 | 21.2 | 46.8 | 400 | s.c. | 883 |
| PG-9 Maleate s.c. | 106 | 123 | 20.6 | 44.2 | 175 | s.c. | 373 |
| SM-32 Oxalate s.c. | 107 | 120 | 16.6 | 37.3 | 260 | s.c. | 584 |

Potency, efficacy and toxicity of SM-21, PG-9 and SM-32 in comparison with four principal reference analgesic drugs tested in mouse. As analgesic test the hot-plate test (52.5° C.) was used.
Efficacy was compared with that of morphine (considered equal to 100). Drug comparison was performed at the highest dose which was found ineffective on rota-rod test (Morphine HCl 8 mg/kg s.c.; Diphenhydramine base 20 mg/kg s.c.; Clomipramine HCl 20 mg/kg s.c.; Ketorolac trometamine 175 mg/kg i.p.; SM-21 maleate 40 mg/kg s.c.; PG-9 maleate 40 mg/kg s.c. and SM-32 oxalate 35 mg/kg s.c.).
M.A.E. = Maximum Analgesic Effect (the comparison was performed considerating the highest peak of analgesia regardless of the time after drug administration).
A.U.C. = Area Under Curve (the comparison was performed considering both the intensity and duration of the analgesic effect).
EE50 = The median effective dose which produced the 50% of analgesic effect obtainable by using the highest dose which was ineffective on the rota-rod test.

TABLE 4

ACETIC ACID WRITHING TEST

| Treatment | number of writhes | percent inhibition | Efficacy as analgesic (Morphine = 100) | ED50 (mg/kg) | ED50 (µmol/kg) |
|---|---|---|---|---|---|
| Saline 10 ml/kg | 34.2 ± 1.4 (18) | 0 | 0 | — | — |
| Morphine HCl 8 mg/kg s.c. | 8.6 ± 1.9* (12) | 74.8 | 100 | 2.7 | 8.4 |
| DFD 20 mg/kg s.c. | 24.6 ± 2.4* (10) | 28.1 | 38 | 7.8 | 30.5 |
| Clom. HCl 20 mg/kg s.c. | 18.2 ± 2.1* (10) | 46.8 | 63 | 9.7 | 27.6 |
| Ketorolac trom. 10 mg/kg i.p. | 6.3 ± 1.4* (10) | 81.6 | 110 | 8.3 | 22.0 |
| Ketorolac trom. 175 mg/kg i.p. | 0.3 ± 0.3* (10) | 99.1 | 133 | 8.3 | 22.0 |
| SM-21 maleate 40 mg/kg s.c. | 11.4 ± 1.6* (13) | 67.3 | 90 | 21.5 | 47.4 |
| PG-9 maleate 40 mg/kg s.c. | 6.1 ± 1.6* (16) | 82.2 | 110 | 16.3 | 34.8 |
| SM-32 oxalate 35 mg/kg s.c. | 5.5 ± 2.1* (10) | 83.4 | 111 | 15.9 | 35.7 |

Effect of SM-21, PG-9 and SM-32 in mouse acetic acid writhing test in comparison with four principal reference analgesic drugs. The test was performed at the highest dose which was ineffective on rota-rod test as shown in Table 1.
ED 50: The median effective dose is that one which produced 50% of analgesic effect obtainable using the highest dose which was ineffective on the rota-rod test. Acetic acid solution = 0.6% v/v.
*$P < 0.01$ compared to saline controls. The number of mice is in parentheses.
Clom. = Clomipramine Ketor. trom. = Ketorolac trometamine; DFD = Diphenhydramine.

TABLE 5

PAW-PRESSURE in rats (g)

| Treatment | Before treatment | After treatment 15 min | After treatment 30 min | After treatment 45 min |
|---|---|---|---|---|
| Saline 10 ml/kg i.p. | 58.0 ± 4.0 (15) | 61.2 ± 6.2 (15) | 59.8 ± 2.2 (15) | 61.6 ± 1.8 (15) |
| Morphine HCl 5 mg/kg i.p. | 56.5 ± 4.5 (10) | 112.3 ± 4.8* (10) | 118.0 ± 5.4* (10) | 107.0 ± 3.8* (10) |
| Diphenhydramine 15 mg/kg i.p. | 64.0 ± 5.8 (5) | 72.6 ± 6.8 (5) | 70.0 ± 5.4 (5) | 68.0 ± 6.6 (5) |
| Clomipramine 25 mg/kg i.p. | 62.3 ± 4.6 (6) | 85.0 ± 6.8^ (6) | 99.0 ± 6.6* (6) | 91.7 ± 7.4^ (6) |
| Ketorolac tromet. 100 mg/kg i.p. | 63.0 ± 4.1 (9) | 59.3 ± 5.6 (9) | 97.4 ± 6.2* (9) | 74.6 ± 5.8 (9) |
| SM-21 maleate 20 mg/kg i.p. | 59.0 ± 4.3 (8) | 93.1 ± 4.0* (8) | 93.4 ± 5.4* (8) | 92.3 ± 6.4^ (8) |
| PG-9 maleate 20 mg/kg i.p. | 54.4 ± 3.0 (8) | 62.2 ± 6.0 (8) | 62.4 ± 4.8 (8) | 62.8 ± 4.2 (8) |
| SM-32 maleate 20 mg/kg i.p. | 56.0 ± 3.1 (7) | 86.2 ± 4.0^ (7) | 92.0 ± 6.1* (7) | 69.0 ± 4.8 (7) |

Effect of SM-21, PG-9 and SM-32 in rat paw-pressure test in comparison with four principal reference analgesic drugs.
The test was performed using the highest dose which did not modify the normal behaviour of rats. In fact the researchers, who were unaware of the treatment received by the animals, were unable to distinguish among the various groups. *$P < 0.01$; ^$P < 0.05$ compared to saline controls. The number of rats is in parentheses. Ketorolac tromet. = Ketorolac trometamine

TABLE 6

| | TAIL-FLICK in rat(s) | | | |
|---|---|---|---|---|
| | Before | After treatment | | |
| Treatment | treatment | 15 min | 30 min | 45 min |
| Saline | 3.1 ± 0.1 | 3.1 ± 0.2 | 2.8 ± 0.1 | 2.7 ± 0.1 |
| 10 ml/kg i.p. | (14) | (14) | (14) | (14) |
| Morphine HCl | 3.1 ± 0.01 | 5.9 ± 0.5* | 8.2 ± 0.6* | 7.8 ± 0.5* |
| 5 mg/kg i.p. | (9) | (9) | (9) | (9) |
| Diphenhydramine | 3.2 ± 0.1 | 2.9 ± 0.2 | 2.5 ± 0.2 | 2.5 ± 0.1 |
| 15 mg/kg i.p. | (9) | (9) | (9) | (9) |
| Clomipr. HCl | 2.7 ± 0.1 | 2.9 ± 0.2 | 2.6 ± 0.1 | 2.6 ± 0.2 |
| 25 mg/kg i.p. | (9) | (9) | (9) | (9) |
| Ketorolac tromet. | 2.8 ± 0.1 | 3.3 ± 0.2 | 3.2 ± 0.2 | 2.6 ± 0.3 |
| 100 mg/kg i.p. | (8) | (8) | (8) | (8) |
| SM-21 maleate | 3.1 ± 0.2 | 3.6 ± 0.2 | 4.6 ± 0.4^ | 4.9 ± 0.4^ |
| 20 mg/kg i.p. | (8) | (8) | (8) | (8) |
| PG-9 maleate | 3.2 ± 0.1 | 3.3 ± 0.2 | 2.9 ± 0.4 | 3.0 ± 0.3 |
| 20 mg/kg i.p. | (8) | (8) | (8) | (8) |
| SM-32 oxalate | 3.2 ± 0.2 | 3.1 ± 0.5 | 4.7 ± 0.6^ | 4.3 ± 0.5^ |
| 20 mg/kg i.p. | (7) | (7) | (7) | (7) |

Effect of SM-21, PG-9 and SM-32 in rat paw-pressure test in comparison with four principal reference analgesic drugs. The test was performed using the highest dose which did not modify the normal behaviour of rats. In fact the researchers, who were unaware of the treatment received by the animals, were unable to distinguish among the various groups. *$P < 0.01$; ^$P < 0.05$ compared to saline controls.
Clomipr. = Clomipramine; Ketorolac tromet. = trometamine
The number of rats is in parentheses.

TABLE 7

| | PAW-PRESSURE in guinea-pig (g) | | | |
|---|---|---|---|---|
| | Before | After treatment | | |
| Treatment | treatment | 15 min | 30 min | 45 min |
| Saline | 44.6 ± 3.6 | 41.4 ± 2.8 | 43.6 ± 3.8 | 42.0 ± 2.4 |
| 10 ml/kg | (10) | (10) | (10) | (10) |
| SM-21 maleate | 40.0 ± 2.2 | 92.8 ± 4.0* | 110.0 ± 6.6* | 64.0 ± 6.2 |
| 20 mg/kg i.p. | (5) | (5) | (5) | (5) |
| PG-9 maleate | 42.0 ± 2.0 | 94.6 ± 4.4* | 83.0 ± 6.8^ | 42.8 ± 5.6 |
| 20 mg/kg i.p. | (4) | (4) | (4) | (4) |

Effect of SM-21 and PG-9 in guinea-pig paw-pressure test. *$P < 0.01$; ^$P < 0.05$ in comparison with saline controls. The number of guinea-pig is in parentheses.

TABLE 8

EFFECT OF SM-21, MORPHINE AND BACLOFEN ON RATS
WITH A LESION IN THE NUCLEUS BASALIS
MAGNOCELLULARIS (NBM) MEASURED USING THE
PAW-PRESSURE TEST

| | PAW-PRESSURE in rats (g) | | | |
|---|---|---|---|---|
| Treatment | Before | After treatment | | |
| i.p. | treatment | 15 min | 30 min | 45 min |
| Saline (naive) | 67.0 ± 3.2 | 68.5 ± 2.0 | 66.4 ± 3.2 | 65.0 ± 3.0 |
| 10 ml/kg | (18) | (18) | (18) | (18) |
| SM-21 (naive) | 62.8 ± 4.0 | 109.6 ± 4.8* | 87.5 ± 5.2^ | 67.8 ± 4.4 |
| 30 mg/kg | (9) | (9) | (9) | (9) |
| SM-21 (sham) | 68.7 ± 4.3 | 104.9 ± 4.6* | 93.4 ± 5.3^ | 63.9 ± 5.1 |
| 30 mg/kg | (6) | (6) | (6) | (6) |
| SM-21 (lesioned) | 67.7 ± 4.4 | 75.1 ± 5.8 | 68.3 ± 4.9 | 67.2 ± 3.9 |
| 30 mg/kg | (8) | (8) | (8) | (8) |

TABLE 8-continued

EFFECT OF SM-21, MORPHINE AND BACLOFEN ON RATS WITH A LESION IN THE NUCLEUS BASALIS MAGNOCELLULARIS (NBM) MEASURED USING THE PAW-PRESSURE TEST

| Treatment i.p. | PAW-PRESSURE in rats (g) | | | |
|---|---|---|---|---|
| | Before treatment | After treatment | | |
| | | 15 min | 30 min | 45 min |
| Morphine (naive) 5 mg/kg | 65.5 ± 3.8 (6) | 82.5 ± 5.8^ (6) | 125.0 ± 4.3* (6) | 124.0 ± 5.2* (6) |
| Morphine (lesioned) 5 mg/kg | 72.4 ± 3.6 (5) | 88.0 ± 4.8^ (5) | 140.4 ± 5.3* (5) | 138.8 ± 5.5* (5) |
| Baclofen (sham) 4 mg/kg | 74.8 ± 4.8 (6) | 108.7 ± 6.6* (6) | 132.8 ± 5.9* (6) | 124.7 ± 5.8* (6) |
| Baclofen (lesioned) 4 mg/kg | 71.0 ± 3.9 (6) | 117.4 ± 6.4* (6) | 137.9 ± 4.8* (6) | 131.8 ± 5.7* (6) |

The number of rats is in parentheses; ^P < 0.05, *P < 0.01 in comparison with saline.
Each value represents the mean of at least 2 experiments.

TABLE 9

$$R_1-(Ar)-X-\underset{\underset{R_5}{|}}{\overset{\overset{R_2}{|}}{C}}-\underset{\overset{||}{O}}{C}-Y-R_3$$

| N. | MARK | Ar | $R_1$ | $R_2$ | $R_5$ | $R_3$[a)] | X | Y | SALT | ANALGESIC ACTIVITY[b)] |
|---|---|---|---|---|---|---|---|---|---|---|
| 1 | $NR_{100}$ | phenyl | 4-F | $CH_3$ | H | A | O | O | Citrate | ++++ |
| 2 | $SM_{15}$ | — | 4-Br | $CH_3$ | H | A | O | O | Oxalate | ++ |
| 3 | $SM_{19}$ | — | 4-$CF_3$ | $CH_3$ | H | A | O | O | Oxalate | + |
| 4 | $NR_{95}$ | — | 4-$SCH_3$ | $CH_3$ | H | A | O | O | Maleate | + |
| 5 | $SS_{26}$ | — | 4-CN | $CH_3$ | H | A | O | O | Maleate | ++ |
| 6 | $SS_{10}$ | — | 3.4-Cl | $CH_3$ | H | A | O | O | Maleate | + |
| 7 | $SM_{12}$ | — | 3-Cl | $CH_3$ | H | A | O | O | Oxalate | ++ |
| 8 | $SM_{21}$ | — | 4-Cl | $C_2H_5$ | H | A | O | O | Maleate | ++++ |
| 9 | $AC_{15}$ | — | 4-F | $C_2H_5$ | H | A | O | O | Citrate | ++++ |
| 11 | $SS_{12}$ | — | H | $CH_3$ | H | A | S | O | Maleate | ++ |
| 12 | $SS_{20}$ | — | 4-Cl | $CH_3$ | H | A | S | O | Maleate | +++ |
| 13 | $SM_{17}$ | — | 4-Br | $CH_3$ | H | A | S | O | Oxalate | ++++ |
| 14 | $SM_{23}$ | — | 4-F | $CH_3$ | H | A | S | O | Oxalate | ++ |
| 15 | $SS_{21}$ | — | 4-$CH_3$ | $CH_3$ | H | A | S | O | Maleate | + |
| 16 | $SM_{32}$ | — | H | $C_2H_5$ | H | A | S | O | Oxalate | ++++ |
| 17 | $SM_{35}$ | — | 4-Cl | $C_2H_5$ | H | A | S | O | Oxalate | +++ |
| 18 | $AC_{11}$ | — | 4-Cl | $CH(CH_3)_2$ | H | A | S | O | Maleate | + |
| 19 | $SS_{29}$ | — | H | $CH_3$ | H | A | NH | O | HCl | +++ |
| 20 | $AC_5$ | — | 4-Cl | $CH_3$ | H | A | NH | O | Oxalate | + |
| 21 | $AC_6$ | — | 4-Cl | $CH_3$ | H | A | $NCH_3$ | O | Maleate | ++ |
| 22 | $AC_{13}$ | — | 4-Cl | $C_2H_5$ | H | A | $NCH_3$ | O | Maleate | ++++ |
| 23 | $SS_{16}$ | — | 4-Cl | $CH_3$ | H | A | O | NH | HCl | + |
| 25 | $PG_8$ | — | 4-Cl | $CH_3$ | H | A | — | O | Maleate | +++ |
| 26 | $PG_9$ | — | 4-Br | $CH_3$ | H | A | — | O | Maleate | ++++ |
| 27 | $PG_4$ | — | 4-$NO_2$ | $CH_3$ | H | A | — | O | HCl | + |
| 28 | $PG_5$ | — | 4-$NH_2$ | $CH_3$ | H | A | — | O | HCl | + |
| 29 | $PG_{18}$ | — | 4-$OCH_3$ | $CH_3$ | H | A | — | O | Maleate | + |
| 30 | $PG_{21}$ | — | 4-F | $CH_3$ | H | A | — | O | Maleate | +++ |
| 31 | $PG_{16}$ | — | 4-$CH_2CHMe_2$ | $CH_3$ | H | A | — | O | Maleate | + |
| 32 | $PG_{13}$ | — | 3-Cl | $CH_3$ | H | A | — | O | Maleate | +++ |
| 33 | $PG_{14}$ | — | 2-Cl | $CH_3$ | H | A | — | O | Maleate | +++ |
| 34 | $PG_{23}$ | — | 2-Br | $CH_3$ | H | A | — | O | HCl | ++ |
| 35 | $PG_{24}$ | — | 4-Br | $C_2H_5$ | H | A | — | O | Maleate | +++ |
| 38 | $SM_{25}$ | — | 4-Cl | $CH_3$ | $CH_3$ | A | O | O | Oxalate | ++ |
| 39 | $GC_9$ | — | 4-Cl | $CH_3$ | H | B | O | O | Maleate | ++ |
| 40 | $GC_{11}$ | — | 4-Cl | $C_2H_5$ | H | B | O | O | Oxalate | ++ |
| 41 | $AC_{19}$ | β-naphtyl | H | $CH_3$ | H | A | O | O | Maleate | +++ |
| 43 | $AC_{31}$ | — | 6-Br | $C_2H_5$ | H | A | O | O | Maleate | + |

TABLE 10

ENANTIOMERS OF RACEMIC PRODUCTS OF TABLE 9

| N. | MARK | $R_1$ | $R_2$ | $R_3$[a] | $R_5$ | X | Y | SALT | ANALGESIC ACTIVITY[b] |
|---|---|---|---|---|---|---|---|---|---|
| 44 | (R) $ET_{142}$(+) | 4-Cl | $CH_3$ | A | H | O | O | Maleate | +++ |
| 45 | (S) $ET_{142}$(−) | 4-Cl | $CH_3$ | A | H | O | O | Maleate | ++ |
| 46 | (R) $SS_{20}$(+) | 4-Cl | $CH_3$ | A | H | S | O | Maleate | +++ |
| 47 | (S) $SS_{20}$(+) | 4-Cl | $CH_3$ | A | H | S | O | Maleate | ++ |
| 48 | (R) $SM_{35}$(+) | 4-Cl | $C_2H_5$ | A | H | S | O | Maleate | +++ |
| 49 | (S) $SM_{35}$(−) | 4-Cl | $C_2H_5$ | A | H | S | O | Maleate | ++ |
| 50 | (R) $NR_{100}$(+) | 4-F | $CH_3$ | A | H | O | O | Citrate | ++++ |
| 51 | (S) $NR_{100}$(−) | 4-F | $CH_3$ | A | H | O | O | Citrate | +++ |
| 52 | (R) $SM_{21}$(+) | 4-Cl | $C_2H_5$ | A | H | O | O | Maleate | |
| 53 | (S) $SM_{21}$(−) | 4-Cl | $C_2H_5$ | A | H | O | O | Maleate | |
| 54 | (R) $SM_{32}$(+) | H | $C_2H_5$ | A | H | S | O | Oxalate | |
| 55 | (S) $SM_{32}$(−) | H | $C_2H_5$ | A | H | S | O | Oxalate | |

Notes of Tables 9 and 10:
[a] A, B and E stand for

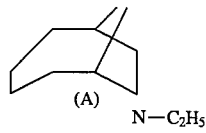
(A)

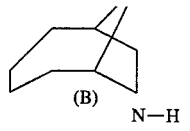
(B)

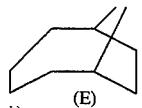
(E)

[b] Degree of analgesia, expresed as latency on hot plate, obtained at max. dose not affecting mice behaviour:
Latency under or equal to 19" inactive
Latency under or equal to 25" +
Latency under or equal to 30" ++
Latency under or equal to 35" +++
Latency above 35" ++++

We claim:
1. Compounds of general formula:

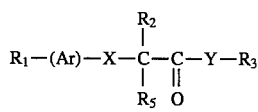

where:
Ar=phenyl or beta-naphthyl;
$R_1$=one or more substituents of the Ar nucleus, and selected from the group consisting of H, $CH_3$, $CH_2$—$CH(CH_3)_2$, O—$CH_3$, Cl, F, Br, $CF_3$, $NH_2$, S—$CH_3$, CN, and $NO_2$ $R_2$=H, $CH_3$, $C_2H_5$, $CH(CH_3)_2$;
$R_3$=

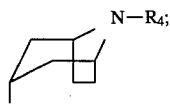

where $R_4$=H, $CH_3$, or $C_2H_5$;
$R_5$=H, or $CH_3$;
X=O, S, NH, $NCH_3$, —CH=CH—, —C≡C—, or a single bond;
Y=O, or NH, both in the racemic form and in the isomeric enantiomeric forms.

2. Compounds according to claim 1, wherein $R_3$ is 3-α-tropanil.

3. Analgesic and nootropic pharmaceutical compositions containing as active ingredient a compound of general formula:

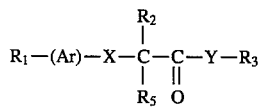

where Ar=phenyl or beta-naphthyl;
$R_1$=one or more substituents of the Ar nucleus, and selected from the group consisting of H, $CH_3$, $CH_2$—CH—$(CH_3)_2$, O—$CH_3$, Cl, F,Br, $CF_3$, $NH_2$, S—$CH_3$, CN, and $NO_2$ $R_2$=H, $CH_3$, $C_2H_5$, or $CH(CH_3)_2$
$R_3$=

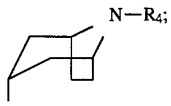

where $R_4$=H, $CH_3$, or $C_2H_5$ $R_5$=H, or $CH_3$

X=O, S, NH, $NCH_3$, —CH=CH—, —CH≡CH—, or a single bond;

Y=O, or NH, both in the racemic form and in the isomeric enantiomeric forms.

4. The pharmaceutical compositions according to claim 3, containing suitable excipients for administration by the oral, intramuscular, subcutaneous, intravenous ways or as suppositories.

5. The composition according to claim 3, wherein the active ingredient is the following compound

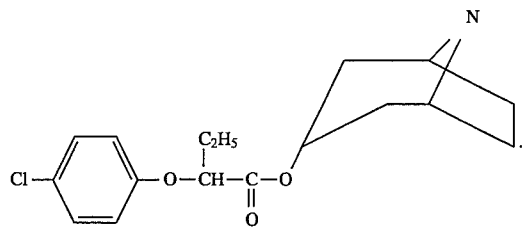

6. The composition according to claim 3, wherein the active ingredient is the following compound

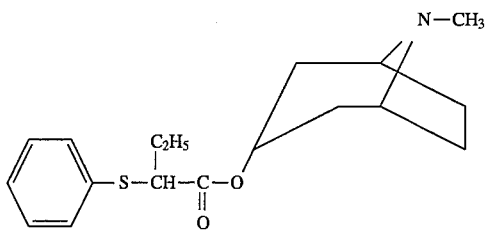

7. The pharmaceutical compositions according to claim 3, wherein the active ingredient is the following compound

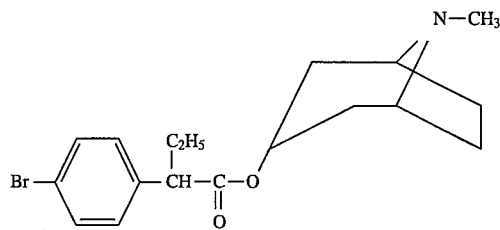

8. A compound according to claim 1 wherein $R_1$ is in the para position.

* * * * *